US012285626B2

(12) United States Patent
Moore-Ede et al.

(10) Patent No.: US 12,285,626 B2
(45) Date of Patent: *Apr. 29, 2025

(54) LIGHTING SYSTEM FOR PROTECTING CIRCADIAN NEUROENDOCRINE FUNCTION

(71) Applicant: Korrus, Inc., Los Angeles, CA (US)

(72) Inventors: Martin Christopher Moore-Ede, Wellesley, MA (US); Rebecca Mary Chacko, Brookline, MA (US); Anneke Marlies Heitmann, Arlington, MA (US); Robert Frederic Casper, Toronto (CA); Robert Frank Karlicek, Jr., Clifton, NY (US); Doros Platika, Pittsburgh, PA (US); Udo Trutschel, Tabarz (DE)

(73) Assignee: KORRUS, INC., Los Angeles, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/108,959

(22) Filed: Feb. 13, 2023

(65) Prior Publication Data
US 2023/0233872 A1 Jul. 27, 2023

Related U.S. Application Data

(63) Continuation of application No. 16/986,123, filed on Aug. 5, 2020, now Pat. No. 11,577,091, which is a
(Continued)

(51) Int. Cl.
A61N 5/06 (2006.01)
A61M 21/00 (2006.01)
(Continued)

(52) U.S. Cl.
CPC ............ *A61N 5/0618* (2013.01); *A61M 21/00* (2013.01); *A61N 5/062* (2013.01); *C09K 11/592* (2013.01);
(Continued)

(58) Field of Classification Search
CPC ...... H05B 47/16; H05B 47/155; H05B 45/20; C09K 11/592; C09K 11/621; F21K 9/20;
(Continued)

(56) References Cited

U.S. PATENT DOCUMENTS 7,520,607 B2 4/2009 Casper
7,678,140 B2 3/2010 Brainard
(Continued)

FOREIGN PATENT DOCUMENTS

CN 101589652 11/2009
CN 101678209 3/2010
(Continued)

OTHER PUBLICATIONS

Bailes, H. J. and R. J. Lucas. 2013. "Human Melanopsin Forms a Pigment Maximally Sensitive to Blue Light (Lambdamax Approximately 479 Nm) Supporting Activation of G(Q/11) and G(i/O) Signaling Cascades." Proceedings. Biological Sciences I the Royal Society 280 (1759): 20122987.
(Continued)

*Primary Examiner* — Alyssa M Alter
*Assistant Examiner* — Jessandra F Hough
(74) *Attorney, Agent, or Firm* — FisherBroyles LLP

(57) ABSTRACT

Lighting systems, methods, and devices for protecting human circadian neuroendocrine function during night use are described. Suitable lighting conditions can be provided for a working environment while protecting the circadian neuroendocrine systems of those occupying the illuminated workplace during the night. Lighting systems, methods, and
(Continued)

devices can provide substantive attenuation of the pathologic circadian disruption in night workers. Lighting systems, methods, and devices can attenuate the specific bands of light implicated in circadian disruption. LED lighting systems, methods, and devices can provide increased intensity at a different portion of the spectrum than conventional LEDs, providing a useable white light even when unfavorable portions of the wavelength are attenuated by a notch filter. LED lighting systems, methods, and devices can switch between a daytime configuration and a night time configuration, wherein the daytime configuration provides unfiltered light and the night time configuration provides filtered light.

20 Claims, 21 Drawing Sheets

Related U.S. Application Data continuation of application No. 15/669,846, filed on Aug. 4, 2017, now Pat. No. 10,786,685, which is a continuation of application No. 14/874,601, filed on Oct. 5, 2015, now Pat. No. 9,827,440, which is a continuation of application No. PCT/US2014/032858, filed on Apr. 3, 2014.

(60) Provisional application No. 61/808,584, filed on Apr. 4, 2013.

(51) Int. Cl.
| | |
|---|---|
| C09K 11/59 | (2006.01) |
| C09K 11/62 | (2006.01) |
| F21K 9/20 | (2016.01) |
| F21V 9/08 | (2018.01) |
| F21V 14/08 | (2006.01) |
| F21Y 105/00 | (2016.01) |
| F21Y 115/10 | (2016.01) |
| F21Y 115/15 | (2016.01) |
| H05B 45/20 | (2020.01) |
| H05B 47/155 | (2020.01) |
| H05B 47/16 | (2020.01) |

(52) U.S. Cl.
CPC ............ *C09K 11/621* (2013.01); *H05B 45/20* (2020.01); *H05B 47/155* (2020.01); *H05B 47/16* (2020.01); *A61M 2021/0005* (2013.01); *A61M 2021/0044* (2013.01); *A61M 2021/0083* (2013.01); *A61M 2205/3368* (2013.01); *A61M 2205/50* (2013.01); *A61N 2005/0629* (2013.01); *A61N 2005/063* (2013.01); *A61N 2005/0636* (2013.01); *A61N 2005/065* (2013.01); *A61N 2005/0651* (2013.01); *A61N 2005/0652* (2013.01); *A61N 2005/0653* (2013.01); *A61N 2005/0654* (2013.01); *A61N 2005/0658* (2013.01); *A61N 2005/0663* (2013.01); *F21K 9/20* (2016.08); *F21V 9/08* (2013.01); *F21V 14/08* (2013.01); *F21Y 2105/00* (2013.01); *F21Y 2115/10* (2016.08); *F21Y 2115/15* (2016.08); *Y02B 20/00* (2013.01); *Y02B 20/30* (2013.01); *Y02B 20/40* (2013.01)

(58) Field of Classification Search
CPC .............. F21Y 2115/10; F21Y 2115/15; F21Y 2105/00; F21Y 2113/00; A61M 2021/0005; A61M 2021/0044; A61M 2021/0083; A61M 2205/3368; A61M 2205/50; A61M 2205/0629; A61M 21/00; A61N 200/0629; A61N 200/063; A61N 200/0636; A61N 200/065; A61N 200/0651; A61N 200/0652; A61N 200/0653; A61N 200/0654; A61N 200/0658; A61N 200/0663; A61N 5/0618; A61N 5/062; F21V 9/08; F21V 14/08
See application file for complete search history.

(56) References Cited

U.S. PATENT DOCUMENTS

| | | |
|---|---|---|
| 7,748,845 B2 | 7/2010 | Casper |
| 9,827,440 B2 | 11/2017 | Moore-Ede |
| 2004/0230252 A1 | 11/2004 | Kullok |
| 2010/0063566 A1 | 3/2010 | Uchiumi |
| 2010/0121420 A1 | 5/2010 | Fiset |
| 2010/0179469 A1 | 7/2010 | Hammond |
| 2010/0244740 A1 | 9/2010 | Alpert |
| 2011/0299277 A1 | 12/2011 | Ehara |
| 2012/0008326 A1 | 1/2012 | Jou |
| 2012/0069551 A1 | 3/2012 | Bues |
| 2012/0167693 A1 | 7/2012 | Asao |
| 2012/0175588 A1 | 7/2012 | Qiao |
| 2012/0200234 A1 | 8/2012 | Godlieb |
| 2012/0271384 A1 | 10/2012 | Muehlemann |
| 2013/0006118 A1 | 1/2013 | Pan |
| 2014/0217417 A1 | 8/2014 | Horie |
| 2014/0217902 A1 | 8/2014 | Maxik |
| 2014/0243935 A1 | 8/2014 | Brainard |
| 2014/0306620 A1 | 10/2014 | Maxik |
| 2015/0102749 A1 | 4/2015 | Soler |
| 2015/0342457 A1 | 12/2015 | Sanchez Ramos |
| 2016/0243379 A1 | 8/2016 | Hommes |
| 2017/0326380 A1 | 11/2017 | Moore-Ede |

FOREIGN PATENT DOCUMENTS

| | | |
|---|---|---|
| CN | 101681330 | 3/2010 |
| CN | 102596302 | 7/2012 |
| CN | 102966899 | 3/2013 |
| CN | 105992612 | 10/2016 |
| EP | 1285676 A2 | 2/2003 |
| EP | 2386329 A1 | 11/2011 |
| EP | 2493541 A2 | 9/2012 |
| JP | 2007044201 | 2/2007 |
| JP | 2009259639 | 11/2009 |
| JP | 2011258649 | 12/2011 |
| JP | 2012064860 | 3/2012 |
| WO | 2000077547 | 12/2000 |
| WO | 2008069101 A1 | 6/2008 |
| WO | 2012110178 | 8/2012 |
| WO | 2013184627 | 12/2013 |
| WO | 2014165692 | 10/2014 |

OTHER PUBLICATIONS

Beaven et al., "A Comparison of Blue Light and Caffeine Effects on Cognitive Function and Alertness in Humans," PLOS One, Oct. 2013, vol. 8, Issue 10, 7 pages.

Berson, D. M., F. A. Dunn, and M. Takao. 2002. "Phototransduction by Retinal Ganglion Cells that Set the Circadian Clock." Science 295: 1070-1073.

Brainard, G. C., D. Sliney, J.P. Hanifin, G. Glickman, B. Byrne, J.M. Greeson, S. Jasser, E. Gerner, and M. D. Rollag. 2008. "Sensitivity of the Human Circadian System to Short-Wavelength (420-Nm) Light." Journal of Biolozical Rhythms 23 (5): 379-86.

Brainard, G. C., J.P. Hanifin, J.M. Greeson, B. Byrne, G. Glickman, E. Gerner, and M. D. Rollag. 2001a. "Action Spectrum for Melatonin Regulation in Humans: Evidence for a Novel Circadian Photoreceptor." The Journal of Neuroscience 21 (16): 6405-6412.

Brainard, G. C., J.P. Hanifin, M. D. Rollag, J. Greeson, B. Byrne, G. Glickman, E. Gerner, and B. Sanford. 2001b. "Human Melatonin

(56) References Cited

OTHER PUBLICATIONS

Regulation is Not Mediated by the Three Cone Photopic-Visual System." Journal of Clinical Endocrinology and Metabolism 86 (1): 433-436.
Cajochen, C., C. Jud, M. Munch, S. Kobialka, A. Wirz-Justice, and U. Albrecht. 2006. "Evening Exposure to Blue Light Stimulates the Expression of the Clock Gene PER2 in Humans." The European Journal of Neuroscience 23 (4): 1082-1086.
Cajochen, C., M. Munch, S. Kobialka, K. Krauchi, R. Steiner, P. Oelhafen, S. Orgul, and A.Wirz-Justice. 2005. "High Sensitivity of Human Melatonin, Alertness, Thermoregulation, and Heart Rate to Short Wavelength Light." Journal of Clinical Endocnnology and Metabolism 90(3): 1311-6.
Chinese Patent Office, Notice of Issuance of Patent Application No. 201480032189.0 dated May 27, 2017 (machine translation), 3 pages.
EP Examination Report in European Application No. 16 762 412.1, dated Mar. 1, 2021, 7 pages.
Japanese Patent Office, Office Action mailed Dec. 13, 2017 for JP Application No. 2016-506622, including English translation of notice of reason for rejection, 13 pages.
Notice of Reason for Rejection, Japanese Patent Application No. 2018-154517, mailed Jul. 10, 2019 (English translation included), 19 pages.
Office Action for Japanese Patent Application No. 2016-506622, mailed Mar. 23, 2018, with English translation of Notice of Reason for Rejection, 8 pages.
Extended European Search Report, dated Jan. 31, 2019, for EP Application No. 18201950.5, 10 pages.
Partial Supplementary European Search Report (R. 164 EPC) dated Oct. 13, 2016 for EP application No. 14778506.7, 8 pages.
Supplementary European Search Report and Written Opinion (R. 62 EPC) dated Jan. 30, 2017 for EP application No. 14778506.7, 14 pages.
The State Intellectual Property Office of the People's Republic of China, office action mailed Dec. 2, 2016 for CN patent application No. 2014800321890, including English translation, 10 pages.
Office Action for Korean Patent Application No. 10-2015-7031686, mailed Mar. 13, 2018, with English translation, 19 pages.
Figueiro, M. G., M. S. Rea, and J. D. Bullough. 2006. "Circadian Effectiveness of Two Polychromatic Lights in Suppressing Human Nocturnal Melatonin." Neurosci Lett 406 (3): 293-7.
Francis, G., L. Bishop, C. Luke, B. Middleton, P. Williams, and J. Arendt. 2008. "Sleep during the Antarctic Winter: Preliminary Observations on Changing the Spectral Composition of Artificial Light." Journal of Sleep Research 17 (3): 354-360.
Gamlin, P. D., D. H. McDougal, J. Pokorny, V. C. Smith, K. W. Yau, and D. M. Dacey. 2007. "Human and Macaque Pupil Responses Driven by Melanopsin-Containing Retinal Ganglion Cells." Vision Res 47 (7): 946-54.
Gooley, J. J., J. Lu, D. Fischer, and C. B. Saper. 2003. "A Broad Role for Melanopsin in Nonvisual Photo reception." Journal of Neuroscience 23: 7093-7106.
Gooley, J. J., K. Chamberlain, K. A. Smith, S. B. Khalsa, S. M. Rajaratnam, E. Van Reen, J.M. Zeitzer, C. A. Czeisler, and S. W. Lockley. 2011. "Exposure to Room Light before Bedtime Suppresses Melatonin Onset and Shortens Melatonin Duration in Humans." Journal of Clinical Endocrinolozy and Metabolism: E463-E72.
Gooley, J. J., S. M. Rajaratnam, G. C. Brainard, R. E. Kronauer, C. A. Czeisler, and S. W. Lockley. 2010. "Spectral Responses of the Human Circadian System Depend on the Irradiance and Duration of Exposure to Light." Science Translational Medicine 2 (31): 3lra33.
Hattar, S., H. W. Liao, M. Takao, D. M. Berson, and K. W. Yau. 2002. "Melanopsin-Containing Retinal Ganglion Cells: Architecture, Projections, and Intrinsic Photo sensitivity." Science 295: 1065-1070.
IN Examination Report in India Application No. 10190/DELNP/2015, dated Aug. 21, 2020, 11 pages.
International Search Report and Written Opinion Issued in PCT/US14/032858, dated Aug. 25, 2014.

Kayumov, L., R. F. Casper, R. J. Hawa, B. Perelman, S. A. Chung, S. Sokalsky, and C. M. Shapiro. 2005. "Blocking Low-Wavelength Light Prevents Nocturnal Melatonin Suppression with no Adverse Effect on Performance during Simulated Shift Work." Journal of Clinical Endocrinology and Metabolism 90 (5): 2755-61.
Kozaki, T., S. Koga, N. Toda, H. Noguchi, and A. Yasukouchi. 2008. "Effects of Short Wavelength Control in Polychromatic Light Sources on Nocturnal Melatonin Secretion." Neuroscience Letters 439 (3): 256-9.
Krames, M. Light-Emitting Diodes: GaN-on-GaN platform removes cost/performance tradeoffs in LED lighting. LaserFocusWorld. Published Sep. 16, 2013. Retrieved Jan. 2020. Retrieved from the Internet URL<https://digital.laserfocusworld.com/laserfocusworld/20 I 309?article_id=1252048&pg=NaN#pgNaN>. 11 pages.
Lin, J. Shuji Nakamura: GaN-on-GaN Will Become the Next Generation LED Technology. LEDinside. Published Apr. 9, 2015. Retrieved Jan. 2020. Retrieved from the Internet: URL<https://www.ledinside.com/interview/2015/4/shuji_nakamura_gan_on_gan_will_become_the_ next generation led technology>. 5 pages.
Lockley, S. W., E. E. Evans, F. A. Scheer, G. C. Brainard, C. A. Czeisler, and D. Aeschbach. 2006. "Short-Wavelength Sensitivity for the Direct Effects of Light on Alertness, Vigilance, and the Waking Electroencephalogram in Humans." Sleep 29 (2): 161-8.
Lockley, S. W., G. C. Brainard, and C. A Czeisler. 2003. "High Sensitivity of the Human CI8 Circadian Melatonin Rhythm to Resetting by Short Wavelength Light." The Journal of Clinical Endocrinolozy and Metabolism 88 (9): 4502-4505.
Mills, P.R., S. C. Tomkins, and L. J. Schlangen. 2007. "The Effect of High Correlated Colour Temperature Office Lighting on Employee Wellbeing and Work Performance." Journal of Circadian Rhythms 5: 2.
Moore-Ede et al., "Circadian Light LED Fixtures Present Insulin Resistance Caused by Exposure to Conventional LED Light at Night", Abstract submitted to Light, Health and Wellbeing Conference, 2017.
Mottram, V., B. Middleton, P. Williams, and J. Arendt. 2011. "The Impact of Bright Artificial White and 'Blue-Enriched' Light on Sleep and Circadian Phase during the Polar Winter." Journal of Sleep Research 20 (1 Pt2): 154-61.
Munch, M., S. Kobialka, R. Steiner, P. Oelhafen, A. Wirz-Justice, and C. Cajochen. 2006. "Wave length-Dependent Effects of Evening Light Exposure on Sleep Architecture and Sleep EEG Power Density in Men." American Journal of Physiology. Regulatory, Integrative and Comparative Physiology 290 (5): RI421-8.
Nakamura, S. et al. History of Gallium-Nitride-Based Light-Emitting Diodes for Illumination. Proceedings of the IEEE, vol. 101, No. 10. Published Oct. 2013. 10 pages.
Office Action received in Canadian Patent Application No. 2,908,659. Dated Jun. 8, 2020. 7 pages.
Office Action received in Chinese Patent Application No. 201710683301.2. Dated May 20, 2020. 10 pages. Translation included.
Office Action received in Chinese Patent Application No. 201710683301.2. Dated Nov. 8, 2019. 22 pages. Translation included.
Panda, S., I. Provencio, D. C. Tu, S.S. Pires, M. D. Rollag, A. M. Castmcci, M. T. Pletcher, et al. 2003. "Melanopsin is Required for Non-Image-Forming Photic Responses in Blind Mice." Science 301: 525-527.
Panda, S., S. K. Nayak, B. Camp, J. R. Walker, J.B. Hogenesch, and T. Jegla. 2005. "Illumination of the Melanopsin Signaling Pathway." Science 307: 600-604.
Panda, S., T. K. Sato, A. M. Castmcci, M. D. Rollag, W. J. DeGrip, J.B. Hogenesch, I. Provencio, and S. A. Kay. 2002. "Melanopsin (Opn4) Requirement for Normal Light-Induced Circadian Phase Shifting." Science 298: 2213-2216.
PHILIPS LUMILEDS, LUXEON Rebel PC Amber Technical Datasheet, 2010, PHILIPS, pp. 1-22.
Program for Transforming Healthcare and Well Being Through Lighting, Illuminating Engineering Society (IES), Annual Meeting, Oct. 22-23, 2016, organized by the Renssalaer Polytechnic Institute (PRI) Lighting Enabled Systems Center, 1 page.
Qiu, X., T. Kumbalasiri, S. M. Carlson, K. Y. Wong, V. Krishna, I. Provencio, and D. M. Berson. 2005. "Induction of Photosensitivity by Heterologous Expression of Melanopsin." Nature 433: 745-749.

(56) References Cited

OTHER PUBLICATIONS

Rahman, S. A., S. Marcu, C. M. Shapiro, T. J. Brown, and R. F. Casper. 2011. "Spectral Modulation Attenuates Molecular, Endocrine, and Neurobehavioral Disruption Induced by Nocturnal Light Exposure." American Journal of Physiology Endocrinology and Metabolism 300 (3): E518-27.

Revell, V. L., J. Arendt, L. F. Fogg, and D. J. Skene. 2006. "Alerting Effects of Light are Sensitive to very Short Wavelengths." Neuroscience Letters 399 (1-2): 96-100.

Revell, V. L., J. Arendt, M. Terman, and D. J. Skene. 2005. "Short-Wavelength Sensitivity of the Human Circadian System to Phase-Advancing Light." Journal of Biological Rhythms 20:270-272.

Sasseville, A., D. Benhaberou-Bmn, C. Fontaine, M. C. Charon, and M. Hebert. 2009. "Wearing Blue-Blockers in the Morning could Improve Sleep of Workers on a Permanent Night Schedule: A Pilot Study." Chronobiology International 26 (5): 913-25.

Sasseville, A., N. Paquet, J. Sevigny, and M. Hebert. 2006. "Blue Blocker Glasses Impede the Capacity of Bright Lightto Suppress Melatonin Production." Journal of Pineal Research 41 (1): 73-78.

Scheer, et al., "Short-Wavelength Sensitivity for the Direct Effects of Light on Alertness, Vigilance, and the Waking . . . " Sleep, Mar. 2006, 9 pages.

Shadab A. Rahman, Shai Marcu, Colin M. Shapiro, Theodore J. Brown, Robert F. Casper. Spectral modulation attenuates molecular, endocrine, and neurobehavioral disruption induced by nocturnal light exposure. Am J Physicol Endocri 1Metab 300: E518-E527, 2011, 10 pages.

Straif, K., R. Baan, Y. Grosse, B. Secretan, F. El Ghissassi, Bouvard V, A. Altieri, L. Benbrahim-Tallaa, and Cogliano V. 2007. "Carcinogenicity of Shift-Work, Painting, and Fire-Fighting." The Lancet Oncolor;zv 8: 1065-1066.

Thapan, K., J. Arendt, and D. J. Skene. 2001. "An Action Spectrum for Melatonin Suppression: Evidence for a Novel Non-Rod, Non-Cone Photoreceptor System in Humans." The Journal of Physiology 535 (Pt 1): 261-267.

Viola, A. U., L. M. James, L. J. Schlangen, and D. J. Dijk. 2008. "Blue-Enriched White Light in the Workplace Improves Self-Reported Alertness, Performance and Sleep Quality." Scandinavian Journal of Work, Environment & Health 34 (4): 297-306.

Warman, V. L., D. J. Dijk, G. R. Warman, J. Arendt, and D. J. Skene. 2003. "Phase Advancing Human Circadian Rhythms with Short Wavelength Light." Neuroscience Letters 342 (1-2): 37-40.

Wood, B., M. S. Rea, B. Plitnick, and M. G. Figueiro. 2013. "Light Level and Duration of Exposure Determine the Impact of Self-Luminous Tablets on Melatonin Suppression." Applied Ergonomics 44 (2): 237-240.

Wright, H. R. and L. C. Lack. 2001. "Effect of Light Wavelength on Suppression and Phase Delay of the Melatonin Rhythm." Chronobiology International 18 (5): 801-808.

Wright, H. R., L. C. Lack, and D. J. Kennaway. 2004. "Differential Effects of Light C38 Wavelength in Phase Advancing the Melatonin Rhythm." Journal of Pineal Research 36: 140-144.

Wright, H. R., L. C. Lack, and K. J. Partridge. 2001. "Light Emitting Diodes can be used to Phase Delay the Melatonin Rhythm." Journal of Pineal Research 31: 350-355.

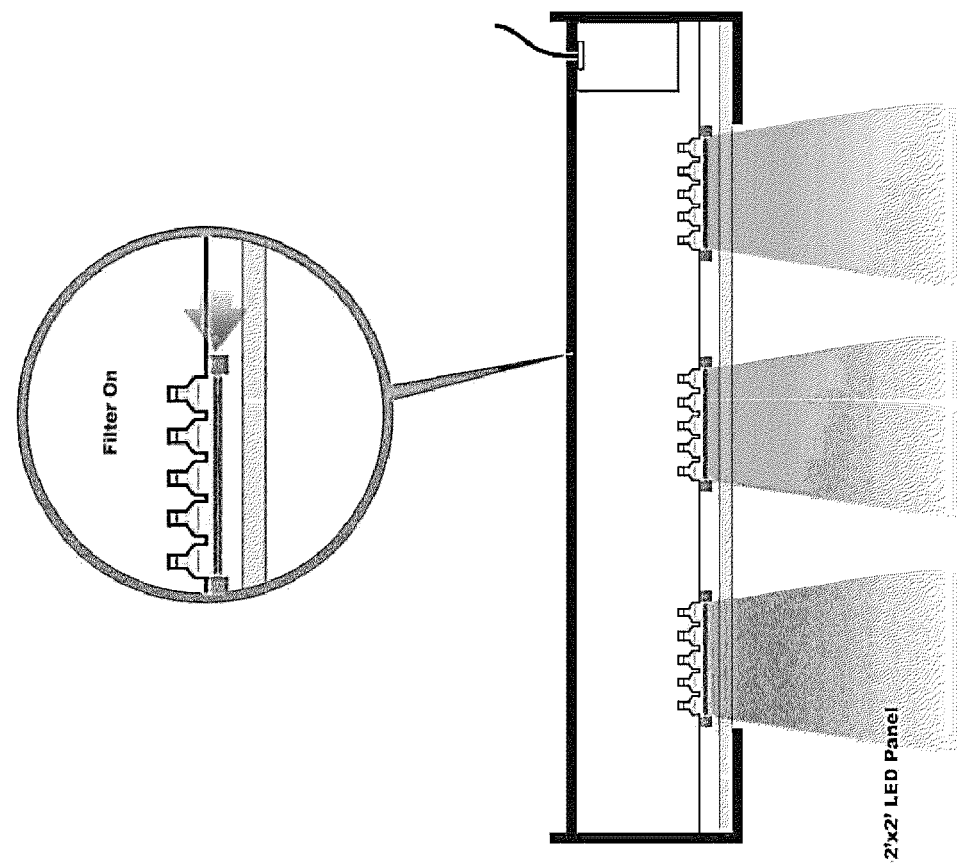
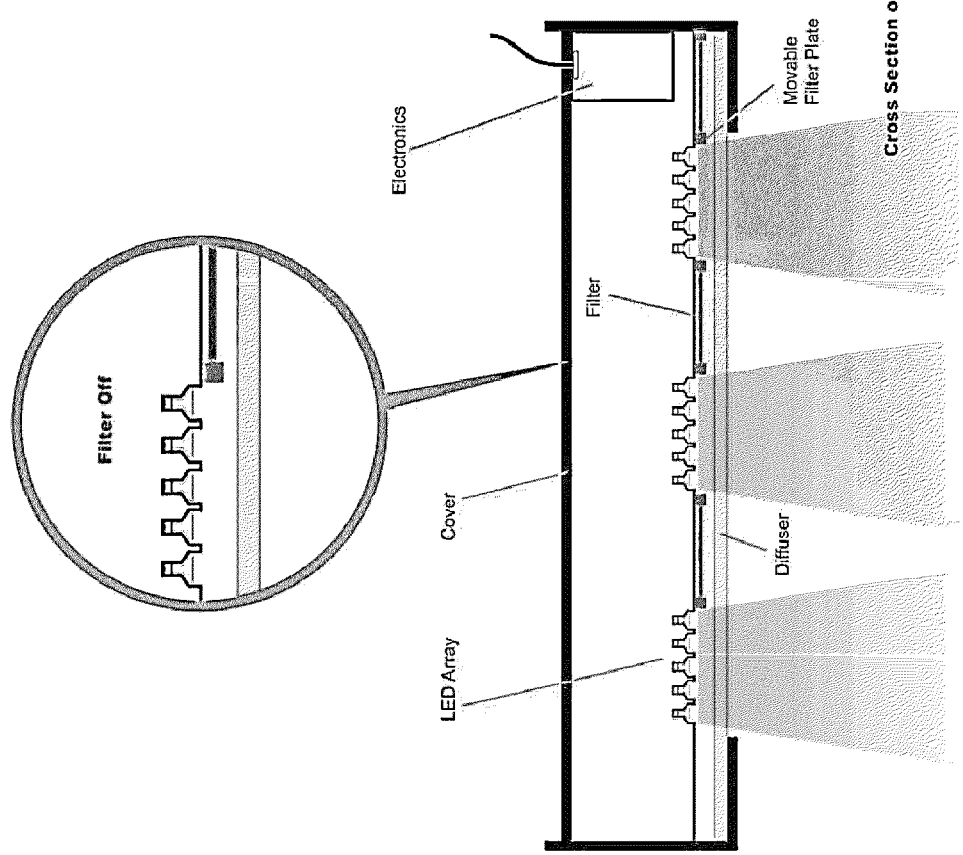
FIG. 6C
FIG. 6D

LIGHTING SYSTEM FOR PROTECTING CIRCADIAN NEUROENDOCRINE FUNCTION

STATEMENT REGARDING FEDERALLY SPONSORED RESEARCH OR DEVELOPMENT

This invention was made with Government support under grant number HL110769 awarded by the National Institute of Health. The Government has certain rights in the invention.

INCORPORATION BY REFERENCE TO RELATED APPLICATIONS

Any and all priority claims identified in the Application Data Sheet, or any correction thereto, are hereby incorporated by reference under 37 CFR 1.57.

BACKGROUND OF THE INVENTION

Field of the Invention

The present invention relates to lighting systems, and in particular, light emitting diode ("LED") lighting systems for protecting circadian neuroendocrine functions, particularly during night use.

Description of the Related Art

Approximately 25% of the workforce in North America is involved in work outside the usual daytime hours. Previous work has shown that night shift work, especially rotating shift work can have detrimental effects both in the short term and long term compared to day shift work. In the short term there is an increased incidence of accidents and impaired job performance due to reduced alertness, while in the long term pathologies linked to shiftwork include cardiovascular disease, metabolic derangements such as obesity, metabolic syndrome and Type II diabetes mellitus; gastrointestinal disease and several different types of cancer, including breast, prostate and colorectal carcinoma, which led the World Health Organization in 2007 to declare shift work as a "probable carcinogen in humans".

These adverse health effects are strongly connected to circadian rhythm disruption due to bright light exposure at night. Circadian rhythms are the approximately 24-hour pattern that is observed in a wide range of physiological functions including, but not limited to, sleep/wake cycle, neuroendocrine rhythms, feeding times, mood, alertness, cell proliferation and even gene expression in various tissue types. These rhythms are regulated by an endogenous (internal) circadian timing system which is synchronized by exposure to daily cycles of environmental (outdoor and indoor) light and darkness, detected by retinoganglion cells in the retina of the eye and transmitted via a retinohypothalmic neural pathway to the master circadian pacemaker ("biological clock") located in the Suprachiasmatic Nuclei (SCN) of the hypothalamus. Exposure to bright light at night can desynchronize the SCN so its phase is altered, causing disruption of sleep-wake patterns and multiple key body neuroendocrine systems which may take days or even weeks to recover leading to fatigue and malaise and poor health.

While some problems faced by shift workers are directly linked to acute and chronic reduction in sleep quantity and quality, chronic circadian disruption as a result of nocturnal light exposure appears to be a key factor in the pathogenesis of some of the medical consequences of shift work. Rodent studies demonstrate that chronic circadian disruption accompanied by little cumulative sleep loss produces acceleration of models of cardiovascular disease, metabolic derangement, and cancer. Recent human laboratory studies have shown that even acute circadian misalignment produces measurable metabolic disruption. Further, in epidemiological studies where both factors have been measured, disturbed sleep in shift work does not appear to account for the increase in cardiovascular risk. Evidence also suggests that light exposure during the biological night results in inhibition of pineal melatonin secretion, and chronic reduction in this oncostatic hormone over years of exposure to shift work may contribute to the increased risk of cancer, particularly breast cancer, seen in women working the night shift.

Melatonin (N-acetyl-5-methoxytryptamine) is an important hormone secreted by the pineal gland which is a key regulator of circadian functions synchronized by the SCN. Melatonin mediates many biological functions, particularly the timing of those physiological functions that are controlled by the duration of light and darkness. Melatonin is synthesized from tryptophan through serotonin, which is N-acetylated by the enzyme n-acetyl transferase or NAT, and then methylated by hydroxyindol-O-methyl transferase. The enzyme NAT is the rate-limiting enzyme for the synthesis of melatonin, and is increased by norepinephrine at the sympathetic nerve endings in the pineal gland. Norepinephrine is released at night or in the dark phase from these nerve endings. Thus, melatonin secretion is influenced strongly by the timing of light and dark exposure.

Melatonin is secreted from the pineal gland with an endogenous circadian rhythm, peaking at night but its secretion is highly light sensitive. Nocturnal light exposure significantly suppresses melatonin secretion. The suppressive effect of light on melatonin varies with differing wavelengths due to the unique spectral sensitivity of melanopsin photoreceptors in the retinal ganglion cells of the eye. Light exposure of relatively short wavelengths between 420 to 520 nm (with peak sensitivity between 440-470 nm) has the most pronounced suppressant effect. Melatonin has been shown to have various functions such as chronobiotic regulation, immunomodulation, antioxidant effects, regulation of the timing of seasonal breeding and oncostatic effects. The oncostatic effects of melatonin have been shown in vitro, and in animal studies showing that constant exposure to light significantly promotes carcinogenesis due to melatonin suppression. Hence, melatonin suppression by nocturnal bright light has been proposed as a key mediator of the adverse effects of rotating shift work.

Furthermore, light at night disrupts many other endocrine networks, most notably glucocorticoids. Glucocorticoids are a class of steroid hormone produced in the cortex of the adrenal glands. Cortisol is the most important human glucocorticoid and is associated with a variety of cardiovascular, metabolic, immunologic, and homeostatic functions. Elevated levels of cortisol are associated with a stress response. Light induces gene expression in the adrenal gland via the SCN-sympathetic nervous system and this gene expression is associated with elevated plasma and brain glucocorticoids. The amount of cortisol present in the serum generally undergoes diurnal variation, with the highest levels present in the early morning, and the lowest levels at night. The magnitude of glucocorticoid release by light is also dose dependently correlated with the light intensity. Light-induced clock-dependent secretion of glucocorticoids may serve an adaptive function to adjust cellular metabolism to the light in a night environment, but also illustrates the presence of stress in response to nocturnal lighting. Elevated glucocorticoids pose numerous health risks including hypertension, psychiatric disorders, insulin resistance and elevated blood sugar levels, and suppression of the immune system. Increased glucocorticoid levels have also been linked with faster proliferation rates of various carcinomas, most notably breast cancer. Elevated levels of cortisol during pregnancy are further associated with metabolic syndrome in offspring. Epidemiological studies in diverse populations have demonstrated an association between low birth weight and the subsequent development of hypertension, insulin resistance, Type 2 diabetes, and cardiovascular disease. This association appears to be independent of classical adult lifestyle risk factors. In explanation, it has been proposed that a stimulus or insult acting during critical periods of growth and development permanently alters tissue structure and function, a phenomenon termed "fetal programming". Intriguingly, there is evidence that this phenomenon is not limited to the first-generation offspring and programming effects may persist in subsequent generations. Epidemiological studies in humans suggest intergenerational effects on birth weight, cardiovascular risk factors, and Type 2 diabetes. Similarly, transgenerational effects on birth weight, glucose tolerance, blood pressure, and the hypothalamic-pituitary-adrenal axis have been reported in animal models. One major hypothesis to explain fetal programming invokes overexposure of the fetus to glucocorticoids. Glucocorticoids exert long-term organizational effects and regulate organ development and maturation. In fact, glucocorticoids are exploited therapeutically in the perinatal period to alter the rate of maturation of organs such as the lung. Glucocorticoid treatment during pregnancy reduces birth weight in animals and humans. Furthermore, cortisol levels are increased in human fetuses with intrauterine growth retardation or in pregnancies complicated by preeclampsia, which may reflect a stress response in the fetus. It has been shown that rats exposed to dexamethasone (synthetic glucocorticoid) during the last third of pregnancy, are of low birth weight and develop hypertension and glucose intolerance in adulthood.

The chronobiotic properties of melatonin help to synchronize circadian rhythms in various body systems. In the absence of melatonin there can be desynchronization of circadian rhythms because the phase or timing of some physiological processes do not align with external time cues. Such an example is the markedly delayed time of sleep onset and offset in patients with Delayed Sleep Phase Syndrome (DSPS), which does not correspond to habitual hours of sleep and activity. These individuals exhibit poor alertness and psychomotor performance when they are made to conform to conventional times of activity. Furthermore, such underlying circadian rhythm misalignment can often manifest itself as overt psychological disorders ranging from subsyndromal depression to major depression.

The presence of depression in DSPS populations has been previously reported. DSPS is characterized by sleep onset insomnia where the patient may spend long hours before being able to fall asleep. It is a Circadian Rhythm Sleep Disorder, caused by a desynchronized central biological clock. It has been reported that DSPS patients showed emotional features such as low self-esteem, nervousness and lack of control of emotional expression. These characteristics may worsen social withdrawal, causing a loss of social cues in synchronizing their circadian rhythm. Thus, the phase shift becomes more profound and a vicious circle continues.

Apart from psychological disorders in individuals with circadian rhythm misalignment, the presence of depression has also been noted in low melatonin secretors. Several studies undertaken in recent years have shown that both the amplitude and rhythm of melatonin secretion is altered in patients suffering from unipolar depression as well as in patients suffering from bipolar affective disorders.

One approach taken in an attempt to improve conditions associated with disruption of the usual light-dark cycle include entrainment of the circadian rhythm to a delayed phase using bright light therapy in the hopes of increasing alertness at night and inducing sleep during morning hours. However, at the end of the night shift exposure to natural outdoor bright daylight serves as a potent circadian time cue ("Zeitgber"), overriding the potentially beneficial effects of bright light interventions and negating circadian rhythm entrainment. Additionally, bright light administered at night disrupts the body's natural circadian melatonin profile by preventing the melatonin secretion at night. Substantial research evidence is emerging to implicate potential long term consequences of shift-work associated risk factors including increased risk of cancer, cardiovascular disease, gastrointestinal disorders and mood disorders and their associated morbidity and mortality. Recent studies implicate melatonin secretion disruption with these risk factors.

Currently available efforts to address this problem fall well short of the goal of a practical, broadly applicable, and effective therapy. For example, pharmacologic treatments of sleepiness and daytime sleep disturbance in shift workers are now available, but there are obvious concerns about the widespread chronic utilization of these medications in the broad shift work population. Moreover, pharmacological treatments of sleep disturbance and sleepiness do not alter the underlying mismatch between the internal circadian timing system and the shift schedule. Recent animal and human data support a model in which the chronic misalignment of behavior and internal timing is at least as important as chronic sleep deprivation in mediating the heightened prevalence of metabolic disease, cardiovascular disease, and cancer seen in shift workers. In theory, this shortcoming could be addressed by manipulations of worker light-dark schedules. Such manipulations have been shown in laboratory simulations to produce improved circadian alignment with the work schedule. However, enhanced workplace lighting is not broadly applicable to the entire array of shift work physical environments and shift work schedules. More limiting, these manipulations typically depend on worker compliance with schedule and light-dark exposure limitations even on days off, and as a consequence have not found widespread acceptance.

There is a need for a simple, effective and inexpensive system to limit the widespread and extensive adverse health effects of light exposure at night, without unduly increasing fatigue or reducing alertness.

Thus, there exists a need for a means to improve shift worker alertness while simultaneously limiting the underlying health consequences of circadian disruption which is broadly applicable to different shift work settings and available to many shift workers, not just those with diagnosable conditions.

SUMMARY OF THE APPLICATION

The systems, methods and devices described herein have innovative aspects, no single one of which is indispensable or solely responsible for their desirable attributes. Without limiting the scope of the claims, some of the advantageous features will now be summarized.

Research suggests that light exposure during the night hours on a shift work schedule has significant adverse impact on the health of the shift worker. The harmful effects of the light may be due to a small component of the blue light fraction of the visual spectrum. The harmful effects of shift work can be reduced by filtering out this component of the light used to illuminate shift work settings. Filtering out the blue light component results in normalization of the rhythms in hormone secretion and increases in alertness and vigilance performance during the night work house.

Different LEDs, depending on their design and power source, can provide varying levels of intensity of light at different wavelengths. In some embodiments, white light is achieved most efficiently using LEDs emitting near-monochromatic blue light (typically in the 440-470 nm range) that are grown on inexpensive sapphire or silicon carbide substrates. The blue LED chip emits a spike of blue near-monochromatic light and the chip is then coated with a phosphor to generate the broader spectrum of light wavelengths necessary to provide a sufficiently white light illumination. Many high efficiency LED chips used in lighting systems act as a pump which increases the intensity of light at approximately 440-470, because of manufacturing limitations which makes other LED chips less efficient. Testing has shown that the intensity spike at around 440 nm in a conventional LED is highly suppressive of melatonin. Testing has also shown that when a notch filter is utilized to attenuate the specific band implicated in circadian disruption, a conventional LED may not offer white light similar to that of unfiltered light. Under some circumstances a conventional LED with a notch filter, for example eliminating light wavelengths below 500 nm, can give a yellow hue which may not be conducive to an efficient working environment in some applications.

In some embodiments, the LED lighting system incorporates violet LEDs which incorporate a pump which increases the intensity of light at approximately 415 nm as opposed to the conventional spike at approximately 440 nm. Testing has shown that when a notch filter is utilized to attenuate the specific band implicated in circadian disruption, the LEDs with the 415 nm pump unexpectedly produces light substantially similar to unfiltered light. This improved filtered light can provide substantive attenuation of the pathologic circadian disruption in night workers while providing a quality light source to keep them alert, productive, and safe in the workplace. The improved filter light can offer increased alertness, increased vigilance, improved cognitive performance, and reduced accidents and injuries.

In some embodiments, the violet LEDs with a 415 nm pump can utilize Gallium Nitride on a matched Gallium Nitride substrate. In some embodiments, the violet light at 415 nm is used to excite phosphor material which results in a violet spike and a valley of blue, which can create a higher color rendition index and luminous efficacy.

Testing has confirmed that spectrum-specific LED lighting solutions are capable of limiting circadian neuroendocrine disruption associated with nocturnal exposure to traditional lighting. In addition, the results showed that filtered light sources can be effective regarding preserving normal nocturnal melatonin patterns in humans while awake at night. According to one exemplary embodiment, the testing showed that lighting produced by an approximately 415 nm violet pump LEDs with a 430-500 nm notch filter is particularly suited to lighting for night shifts as it minimizes exposure to the spectral range responsible for disruption of nocturnal melatonin patterns and provides suitable light for working conditions. Narrower or different ranges of blocked wavelengths, such as those discussed herein, can further enhance the spectrum of light produced while maintaining the desired melatonin effect and desired conditions for particular environments when applied to a light source that has sufficient light intensity at desired wavelengths.

Embodiments herein generally relate to lighting systems, methods, and devices for protecting human circadian neuroendocrine function during night use. In some aspects, the systems, devices, and methods provide suitable lighting conditions for a working environment while protecting the circadian neuroendocrine systems of those occupying the illuminated workplace during the night. In some aspects, LED lighting systems, methods, and devices are adapted to provide substantive attenuation of the pathologic circadian disruption in night workers. In some aspects, the LED lighting systems, methods, and devices are adapted to attenuate the specific bands of light implicated in circadian disruption. In some aspects, the LED lighting systems, methods, and devices are adapted to provide increased intensity at a different portion of the spectrum than conventional LEDs, providing a useable white light even when unfavorable portions of the wavelength are attenuated by a notch filter. In some aspects, the LED lighting systems, methods, and devices are adapted to switch between a daytime configuration and a night time configuration, wherein the daytime configuration provides unfiltered light and the night time configuration provides filtered light.

One non-limiting embodiment of the present disclosure includes an LED lighting system comprising a plurality of LEDs and a notch filter, wherein the plurality of LEDs include a spike of intensity at approximately 415 nm, and wherein the notch transmits less than 1% of the light between 430 nm and 500 nm.

Another non-limiting embodiment of the present disclosure includes an LED lighting system comprising a plurality of LEDs and a notch filter, wherein the plurality of LEDs include a spike of intensity in the approximate range of 380-430 nm, and wherein the notch transmits less than 1% of the light between one of the following ranges: between about 420 nm and 500 nm; between about 425 nm and 500 nm; between about 430 nm and 500 nm; between about 440 nm and 500 nm; between about 450 nm and 500 nm; between about 460 nm and 500 nm; between about 420 nm and 490 nm; between about 430 nm and 490 nm; between about 440 nm and 490 nm; between about 450 nm and 490 nm; between about 460 nm and 490 nm; between about 420 nm and 480 nm; between about 430 nm and 480 nm; between about 440 nm and 480 nm; between about 450 nm and 480 nm; between about 460 nm and 480 nm; between about 420 nm and 470 nm; between about 430 nm and 470 nm; between about 440 nm and 470 nm; between about 450 nm and 470 nm; between about 420 nm and 460 nm; and between about 440 nm and 460 nm.

Another non-limiting embodiment of the present disclosure can include a plurality of LEDs which include a spike of intensity in the approximate range of 400-420 nm.

Another non-limiting embodiment of the present disclosure can include plurality of LEDs can include a spike of intensity at approximately 415 nm.

Another non-limiting embodiment of the present disclosure includes a method of lighting workplace during the night comprising providing an LED light source, wherein the LED light source provides unfiltered light during the day, and wherein the LED light source provides filtered light during the night.

Another non-limiting embodiment of the present disclosure relates to methods of manufacturing the systems, devices, and components described herein.

Another non-limiting embodiment of the present disclosure relates to methods of using the systems, devices, and components described herein.

Another non-limiting embodiment relates to a means for maintaining the circadian rhythm of workers in a workplace during the night while providing adequate illumination for a safe and productive working environment.

Another non-limiting embodiment of the present disclosure relates to systems and methods for an artificially illuminated environment system adapted for one or more people to be situated therein. A defined environment space is provided. An artificial light source is adapted to deliver light within the defined environment space. The artificial light source is configured such that after taking into account any natural light sources present that deliver light within the defined environment space of the artificially illuminated environment, and after taking into account features of any environmental components present within the defined environment space of the artificially illuminated environment, such as optics, spectral reflectivity of surfaces, and/or properties of materials in the defined environment space that fluoresce, the artificial light source in combination with any contributing natural light sources and/or environmental components delivers between about fifty (50) and about two thousand (2,000) lux of light in the visible light range (about 400 nm to about 700 nm) at between about two (2) and about seven (7) feet above a floor level of the defined environment space. A Circadian Night Mode (CNight Mode) in which light is delivered in a selected bioactive wavelength band range preferably does not exceed an average irradiance of about 1 μWatts/cm2 when measured in any direction, wherein the selected bioactive wavelength band range spans at least about 10 nm, and wherein the selected bioactive wavelength band range falls within a general wavelength band range of between about 430 nm and about 500 nm. In some embodiments, the selected bioactive wavelength band range in the CNight Mode preferably does not exceed an average irradiance selected from a group consisting of: about 0.7 μWatts/cm2, about 0.5 μWatts/cm2, about 0.2 μWatts/cm2, and about 0.1 μWatts/cm2, when measured in any direction.

Another non-limiting embodiment of the present disclosure relates to systems and methods for a lighting system that comprises an artificial light source. The artificial light source delivers light in the visible light range (about 400 nm to about 700 nm), and includes a Circadian Night Mode (CNight Mode) in which light delivered in a selected bioactive wavelength band range delivers less than six percent (6%) of the total irradiance from the artificial light source in the visible light range. The selected bioactive wavelength band range can deliver an irradiance selected from a group consisting of: less than four percent (4%), less than two percent (2%), and less than one percent (1%), of the total irradiance from the artificial light source in the visible light range. The CNight Mode violet light is provided in a wavelength band selected from a group consisting of: between about 400 and about 440 nm, between about 400 and about 435 nm, between about 400 and about 430 nm, between about 400 and about 425 nm, and between about 400 and about 415 nm, and that has an average irradiance selected from a group consisting of: greater than about four percent (4%), greater than about six percent (6%), and greater than about ten percent (10%), of the total irradiance from the light source in the visible light range. The CNight Mode preferably alternates with a Circadian Day Mode (CDay Mode) wherein the selected bioactive wavelength band range delivers an irradiance selected from a group consisting of: greater than about four percent (4%), greater than about six percent (6%), and greater than about ten percent (10%), of the total irradiance from the light source in the visible light range. The system can be configured to transition automatically between the CDay Mode and the CNight Mode in response to predetermined circadian-phase or time of day instructions. The duration and timing of CDay and the duration and timing of CNight can be preset by the user. The predetermined circadian-phase or time of day instructions may be selected from a group consisting of: instructions including seasonal adjusted times, instructions including fixed clock times, and instructions including times chosen by a user.

Another non-limiting embodiment of the present disclosure relates to systems and methods for a lighting system that comprises a light source. The light source preferably is configured to emit light having a spectral distribution pattern with a violet spike between about 400 nm and about 430 nm, and in some embodiments, between about 400 nm and about 440 nm. A notch filter can be adapted to be coupled to the light source. The notch filter can be configured to filter light emitted by the light source such that a bioactive wavelength band delivers less than about six percent (6%) of the total irradiance from the light source in the visible light range in a first filtered configuration corresponding to a CNight spectral distribution pattern. In some embodiments, a bioactive wavelength band can deliver an irradiance selected from a group consisting of: less than six percent (6%), less than four percent (4%), less than two percent (2%), and less than one percent (1%), of the total irradiance from the light source in the visible light range. A second non-filtered configuration corresponds to a CDay spectral distribution pattern. The bioactive wavelength band can deliver more than about four percent (4%) of the total irradiance from the light source in the visible light range in some embodiments.

Another non-limiting embodiment of the present disclosure relates to systems and methods having a light source that comprises a plurality of discrete wavelength emitting LED chips. The plurality of LED chips together constitute a full visual light spectrum, in a CDay mode. In some embodiments, one or more of the discrete wavelength emitting LED chips is configured to be selectively switched off in a CNight mode such that a bioactive wavelength band delivers less than one percent (1%) of the total irradiance from the light source in the visible light range. In some embodiments, a bioactive wavelength band can deliver an irradiance selected from a group consisting of: less than six percent (6%), less than four percent (4%), less than two percent (2%), and less than one percent (1%), of the total irradiance from the light source in the visible light range. One or more of the LED chips can be monochromatic. In some embodiments, one or more of the LED chips are near-monochromatic. The full visual light spectrum preferably comprises discrete wavelength chips for Violet, Blue, Green, Yellow and Red wavelengths in some embodiments. A Blue LED chip is preferably configured to be selectively switched off in the CNight mode.

Another non-limiting embodiment of the present disclosure relates to systems and methods for a light source that comprises first and second separately-controlled sets of violet LED chips. The first set of violet LED chips is configured to be switched on in a CDay mode and is coated with phosphors which absorb violet light and emit a visible light spectrum across the 400-700 nm range. In some embodiments, the second set of LED chips is configured to be switched on in a CNight mode and is coated with a different phosphor or combinations of phosphors which limit light in a bioactive wavelength band so that the bioactive wavelength band delivers less than one percent (1%) of the total irradiance from the light source in the visible light range. In some embodiments, a bioactive wavelength band can deliver an irradiance selected from a group consisting of: less than six percent (6%), less than four percent (4%), less than two percent (2%), and less than one percent (1%), of the total irradiance from the light source in the visible light range. The day-night pattern lighting can be achieved by switching between the first and second sets of phosphor-coated LEDs. In some embodiments, the coating materials used on the violet LED chips are not conventional rare earth phosphors but have similar absorption and emission characteristics. The coating materials used on the violet LED chips can include colloidal quantum dots and/or alkyl nanocrystals.

Another non-limiting embodiment of the present disclosure relates to systems and methods for a lighting system that comprises a light source comprising a plurality of LED chips that emit light through first and second channels. In some embodiments, the first channel is coated with a phosphor or set of phosphors that during the CNight mode limits light transmission in a bioactive wavelength band so that the bioactive wavelength band delivers less than one percent (1%) of the total irradiance from the light source in the visible light range. In some embodiments, a bioactive wavelength band can deliver an irradiance selected from a group consisting of: less than six percent (6%), less than four percent (4%), less than two percent (2%), and less than one percent (1%), of the total irradiance from the light source in the visible light range. The second channel is configured to be switched on during the CDay mode and has no phosphor coating. The bioactive wavelength band in the CDay mode delivers more than 4% of the total irradiance from the light source in the visible light range in some embodiments. The bioactive wavelength band in the CDay mode can deliver an irradiance selected from a group consisting of: greater than six percent (6%), and greater than 10 percent (10%), of the total irradiance from the light source in the visible light range.

Details of one or more implementations of the subject matter described in this specification are set forth in the accompanying drawings and the description below. Other features, aspects, and advantages will become apparent from the description, the drawings, and the claims. Note that the relative dimensions of the following figures may not be drawn to scale.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 6C illustrates a side view of one embodiment of a LED lighting system including LED arrays in an unfiltered position.

FIG. 6D illustrates a side view of one embodiment of a LED lighting system including LED arrays in a filtered position.

DETAILED DESCRIPTION OF THE PREFERRED EMBODIMENTS

Figure 1A:
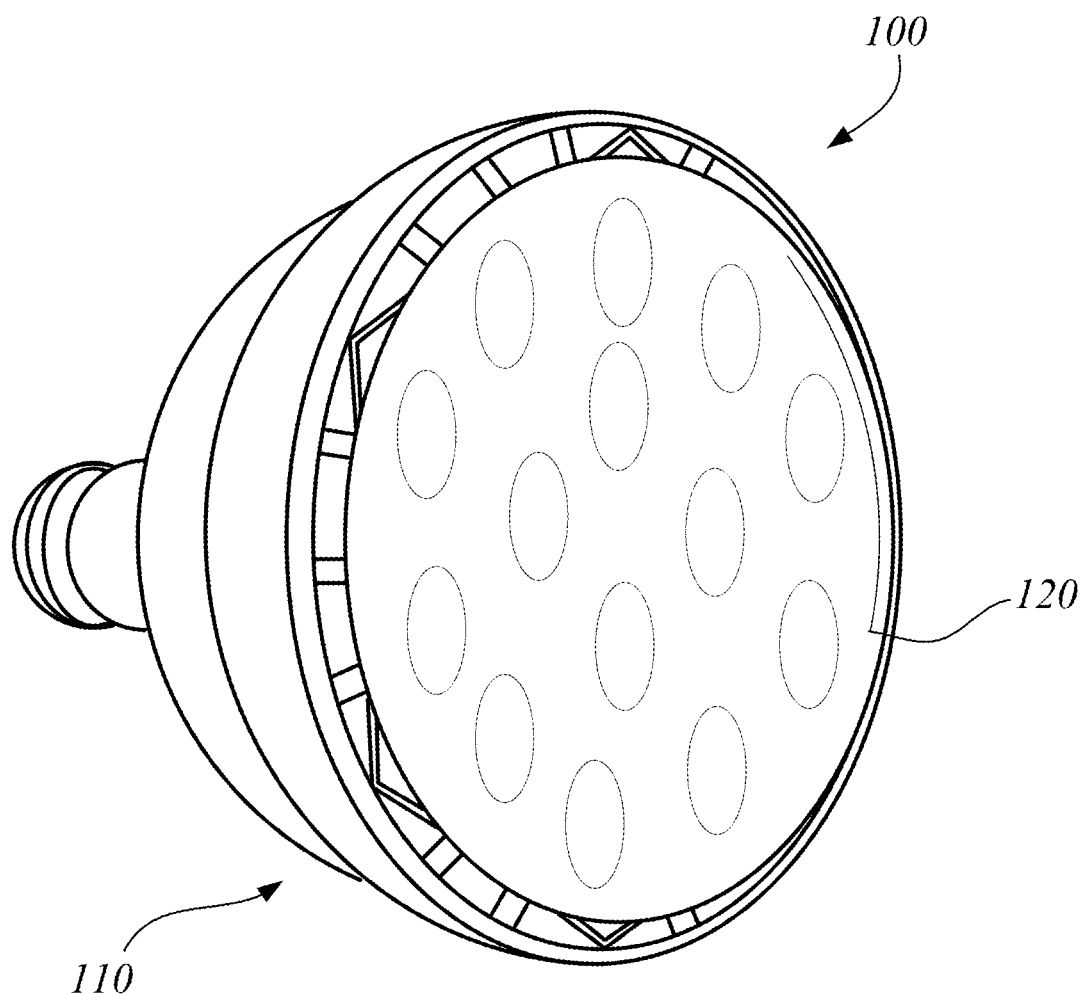
FIG. 1A illustrates a perspective view of one embodiment of a lighting system including a PAR38 LED.

In the following detailed description, reference is made to the accompanying drawings, which form a part of the present disclosure. The illustrative embodiments described in the detailed description, drawings, and claims are not meant to be limiting. Other embodiments may be utilized, and other changes may be made, without departing from the spirit or scope of the subject matter presented here. It will be readily understood that the aspects of the present disclosure, as generally described herein, and illustrated in the Figures, can be arranged, substituted, combined, and designed in a wide variety of different configurations, all of which are explicitly contemplated and form part of this disclosure. For example, a system or device may be implemented or a method may be practiced using any number of the aspects set forth herein. In addition, such a system or device may be implemented or such a method may be practiced using other structure, functionality, or structure and functionality in addition to or other than one or more of the aspects set forth herein. Alterations and further modifications of the inventive features illustrated herein, and additional applications of the principles of the disclosure as illustrated herein, which would occur to one skilled in the relevant art and having possession of this disclosure, are to be considered within the scope of the disclosure.

The advantages of the present disclosure may be accomplished by various means. The following provides a definition for some of the terms used in the specification:

"Circadian rhythm" is a broad term and is used herein in its ordinary sense, and, for example, generally refers to the cycle of approximately 24 hours in the physiological processes of living organisms. As discussed above, the master circadian pacemaker (biological clock) in mammals is located in the Suprachiasmatic Nuclei (SCN), a group of cells located in the hypothalamus. The SCN receives information about illumination through the eyes. The retina of each eye contains special photoresponsive retinal ganglion cells (RGCs) along with traditional photoresponsive rods and cones. These RGCs contain a photo pigment called melanopsin, and information about the timing of environmental light and dark falling on the eyes is transduced by the RCG melanopsin photopigment and conveyed through a neural pathway called the retinohypothalamic tract, leading to the SCN.

Research in basic and human circadian physiology has characterized this distinct non-visual photosensory pathway (NVPP) to the endogenous circadian clock and other brain regions. Several studies have demonstrated that filtering short-wavelength (blue) light (<530 nm) from polychromatic white light attenuated nocturnal light-induced suppression of melatonin secretion. Recent work, has shown that filtering specific, bands of the blue light spectrum (<480 nm) that differentially affect this system can normalize markers of circadian disruption including melatonin, cortisol and clock gene expression in rats exposed to nocturnal light. Similar treatments in human subjects, using eyewear with low pass filters of light wavelengths <480 nm, produce equivalent preservation of endocrine and clock-gene rhythms with improvements in measures of alertness and cognitive performance during simulated night shifts, and this has recently been confirmed in field trials with the nurses and nuclear power plant control room operators on 12-hour night shifts.

Circadian rhythms are found in cells in the body outside the SCN master clock, in other words the expression of genes in various tissues throughout the body also follows a circadian rhythm pattern. In the context of the present disclosure, a "clock gene" is a broad term and is used herein in its ordinary sense, and, for example, generally refers to a gene that follows such an expression pattern and is responsible for maintaining circadian oscillations in a specific cellular physiology. It is estimated that about 25% of the human genome shows such a periodicity in expression.

In the context of the present disclosure, a "bioactive band" or "bioactive wavelength band" is a broad term and is used herein in its ordinary sense, and, for example, generally refers to wavelengths of the visible light spectrum within the range of about 430-500 nm or subdivisions of the range which are described herein and where this disclosure describes the effects of reducing irradiance in this wavelength band.

In the context of the present disclosure, "protecting circadian neuroendocrine function" of a subject is a broad term and is used herein in its ordinary sense, and, for example, generally refers to maintaining the amplitude, phase and periodicity of the circadian oscillations observed in physiological processes including, but not limited to, melatonin and cortisol secretion and clock gene expression that would be present in the subject exposed to the geophysical light/dark cycle.

"Normalizing levels" of the expression product of a clock gene is a broad term and is used herein in its ordinary sense, and, for example, generally refers to either increasing or decreasing the level of expression so as to more closely correspond to the levels of the product that would be found in the same subject exposed to a regular geophysical light/dark cycle. More particularly, with respect to melatonin, it refers to maintaining at least 50% of the level in the same individual kept in darkness.

In the present disclosure, normalizing the levels of melatonin involves increasing the level of melatonin as compared to the level that would otherwise be present in a subject exposed to light at night. In the context of cortisol, it involves decreasing the level of cortisol as compared to the level that would otherwise be present in a subject exposed to light at night.

In reference to the present disclosure, the "subject" is a broad term and is used herein in its ordinary sense, and, for example, generally is a mammal, preferably a human. There may be particular advantages conferred where the subject is a female human subject and even more advantages where the subject is pregnant.

"About" is a broad term and is used herein in its ordinary sense, and, for example, generally in the context of wavelength ranges refers to +/−5 nm. In the context of the present disclosure, a "filter" is a broad term and is used herein in its ordinary sense, and, for example, generally is a device that substantially blocks a range of non-transmitted wavelengths of light.

"Retinal exposure" is a broad term and is used herein in its ordinary sense, and, for example, generally refers to light impingement upon the retina of a subject.

"Night" is a broad term and is used herein in its ordinary sense, and, for example, generally refers to the natural hours of darkness and, more specifically, to the dark phase of the geophysical light/dark cycle. In summer, in peri-equatorial latitudes, this is roughly equivalent to about 2100 hrs (9 pm) to about 0600 hr (6 am), which are the peak hours of melatonin production. "During the night" is a broad term and is used herein in its ordinary sense, and, for example, generally refers to any time during this period; preferably, the method of the present disclosure is practiced throughout the night.

"Circadian Night" is a broad term and is used herein in its ordinary sense, and, for example, generally refers to the nocturnal phase of an individual's biological clock and circadian rhythms whether or not the individual is synchronized to the environmental day/night cycle of light and darkness.

"Circadian Day" is a broad term and is used herein in its ordinary sense, and, for example, generally refers to the daytime phase of an individual's biological clock and circadian rhythms whether or not the individual is synchronized to the environmental day/night cycle of light and darkness.

In the context of the present disclosure, lighting systems or other luminaires may be designed to provide certain characteristics during the Circadian Day and other characteristics during the Circadian Night to take account of the different responsiveness of biological systems to light during the Circadian Day versus the Circadian Night. Alternatively, lighting systems may have certain characteristics during the Day and other characteristics during the Night to take account of the different responsiveness of biological systems to light during the Day versus the Night.

"Circadian Day Mode" (or "CDay Mode") is a broad term and is used herein in its ordinary sense, and, for example, generally refers to a lighting system or other luminaire that is configured to provide lighting with the characteristic properties that are appropriate for the Circadian Day.

"Circadian Night Mode" (or "CNight Mode") is a broad term and is used herein in its ordinary sense, and, for example, generally refers to a lighting system or other luminaire that is configured to provide lighting with the characteristic properties that are appropriate for the Circadian Night.

"Pump" is a broad term and is used herein in its ordinary sense, and, for example, generally refers to a quality of the LED chip which generates a high intensity spike of light within a defined range within the spectrum of light.

Research suggests that light exposure during the night hours on a shift work schedule has significant adverse impact on the health of the shift worker. The harmful effects of the light may be due to a small component of the blue light fraction of the visual spectrum. The harmful effects of shift work can be reduced by filtering out this component of the light used to illuminate shift work settings. Filtering out the blue light component results in normalization of the rhythms in hormone secretion and increases in alertness and vigilance performance during the night work house. U.S. Pat. No. 7,520,607 to Casper et al. and U.S. Pat. No. 7,748,845 to Casper et al. describe devices and methods for blocking retinal exposure to particular wavelengths of light and are hereby incorporated by reference in their entirety. Rahman et al. describes how spectral modulation attenuates the negative physiological effects of unfiltered light exposure at night, Shadab A. Rahman, Shai Marcu, Colin M. Shapiro, Theodore J. Brown, Robert F. Casper. Spectral modulation attenuates molecular, endocrine, and neurobehavioral disruption induced by nocturnal light exposure. *Am J Physiol Endocrinal Metab* 300: E518-E527, 2011 which is hereby incorporated by reference in its entirety. In addition, attached herewith are the materials incorporated by reference herein and which form part of the present disclosure.

As described below, in some embodiments, a more effective approach is now possible. Recent research has identified a distinct non-visual photosensory pathway (NVPP) to the endogenous circadian clock and other brain regions. This system is anatomically and functionally distinct from the pathways mediating conscious vision. Specifically, the action spectrum of the photoreceptors involved is different from that of the rods and cones of vision. Filtering specific, narrow bands of the visual light spectrum can normalize markers of circadian disruption including melatonin, cortisol, and clock gene expression in subjects exposed to nocturnal light. Eyewear with low pass filters filtering out wavelengths less than 480 nm have produced equivalent preservation of endocrine and clock-gene rhythms with improvements in measures of alertness and cognitive performance during simulated night shifts. These results have also been confirmed in field trials in nurses and nuclear power plant control room operators on 12-hour night shifts. Beyond immediate improvements in alertness and performance, the preservation of normal circadian organization, including normal melatonin secretion, should translate into meaningful attenuation of health risks associated with chronic circadian disruption in night shift work.

Embodiments described herein generally relate to systems, devices, and methods related to lighting systems. More specifically, some embodiments relate to spectrum-specific, indoor LED lighting systems that provide usable indoor illumination absent the spectral components that are associated with circadian disruption. In some other embodiments lighting systems other than LED lighting systems can also be used. For example, lighting sources that can provide the desired light intensity in particular wavelength ranges can be used in some embodiments. In some embodiments, the LED lighting systems can be used at night without producing significant circadian disruption, providing immediate improvements in alertness and performance and the potential for long-term improvements in shift worker health, and can have significant potential application in the large and growing segment of the modern economy that requires night work.

Figure 1B:
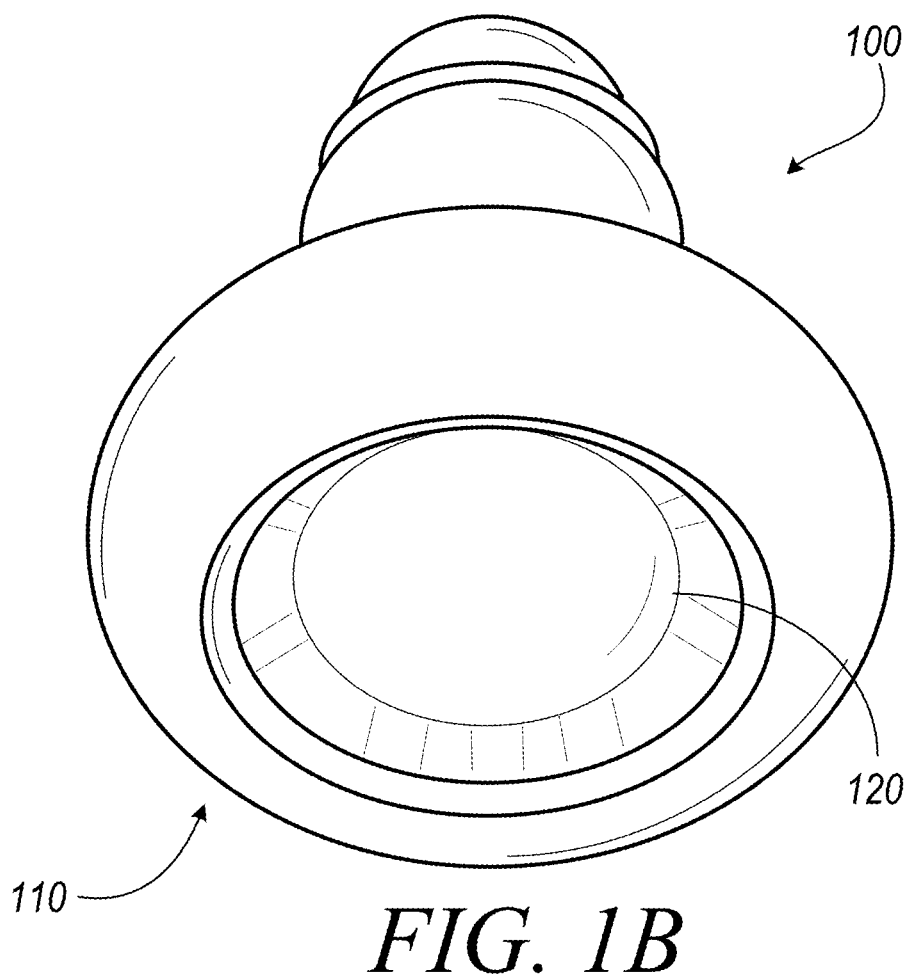
FIG. 1B illustrates a perspective view of on embodiment of a lighting system including a MR16 LED.
Figure 3:
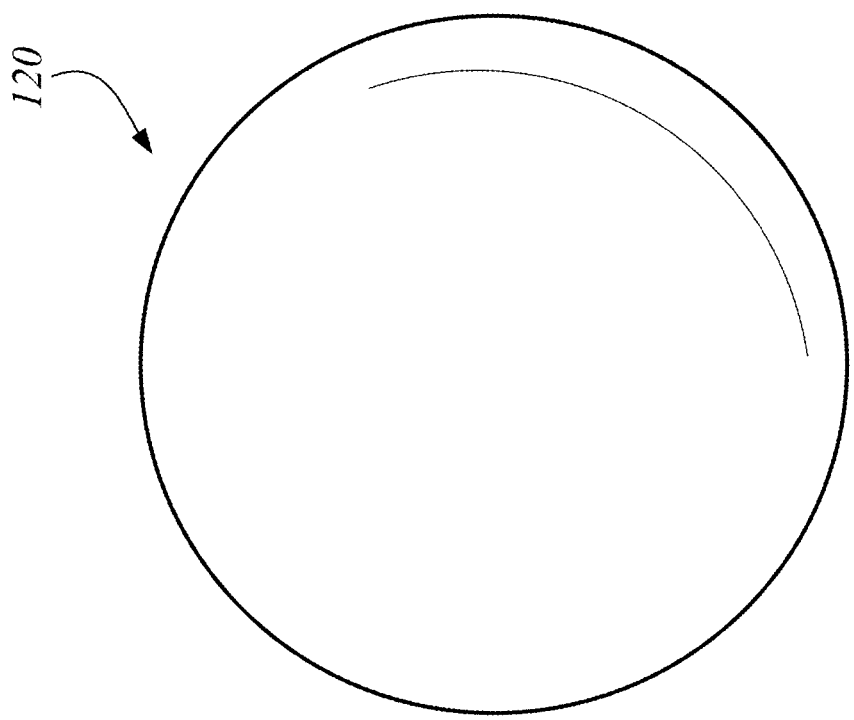
FIG. 3 illustrates a top view of one embodiment of a notch filter.
Figure 2:
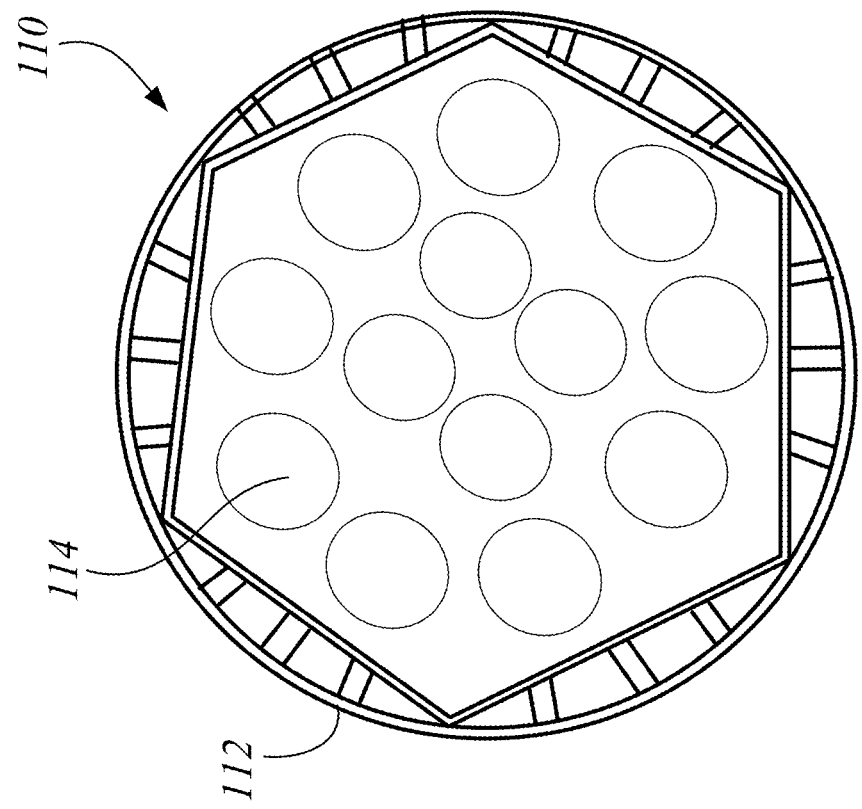
FIG. 2 illustrates a perspective view of one embodiment of a LED light.

FIG. 1A illustrates a perspective view of one embodiment of a lighting system 100 including a PAR38 LED. FIG. 1B illustrates a perspective view of on embodiment of a lighting system 100 including a MR16 LED. FIG. 2 illustrates a perspective view of one embodiment of a LED light 110. FIG. 3 illustrates a top view of one embodiment of a notch filter 120. In some embodiments, the LED lighting system 100 can include a LED light 110 and a notch filter 120 to remove the harmful portion of the light spectrum. In some embodiments the LED light 110 can include a PAR38 LED. In some embodiments the LED light 110 can include an MR16 LED. In some embodiments, the LED light 110 can include an LED array. In some embodiments, the LED light 110 can include other types of LED's known to those in the art. The LED light 110 can include a housing 112 and a plurality of LEDs 114. The housing 112 can orient the LEDs 114 in the preferred configuration and connect the LEDs 114 to a power source. In some embodiments, the housing 112 can also couple the notch filter 120 to the LED light 110. In some embodiments, the LED lighting system 100 can substantially block the specific band implicated in circadian disruption, which may include, for example, approximately 460-480 nm, but still provide functional near-white illumination. The LED lighting system 100 can provide substantive attenuation of the pathologic circadian disruption in night workers, regardless of workplace environment and work schedule. Those skilled in the art will appreciate that the embodiments described herein could use other light sources instead of LEDs, which may include, for example, halogen or fluorescent light. In some embodiments, as illustrated in FIG. 1A, the LED light 110 can be a Par38 LED. In some embodiments, as illustrated in FIG. 1B, the LED light 110 can be a MR16 LED.

In some embodiments, the LED lighting system 100 includes spectroscopic notch filters 120. In some embodiments, the notch filter 120 attenuates a filtered range of transmission to less than 40% of total spectral power. In some embodiments, the notch filter 120 attenuates a filtered range of transmission to less than 40% of total spectral power. In some embodiments, the notch filter 120 attenuates a filtered range of transmission to less than 30% of total spectral power. In some embodiments, the notch filter 120 attenuates a filtered range of transmission to less than 20% of total spectral power. In some embodiments, the notch filter 120 attenuates a filtered range of transmission to less than 10% of total spectral power. In some embodiments, the notch filter 120 attenuates a filtered range of transmission to less than 5% of total spectral power. In some embodiments, the notch filter 120 attenuates a filtered range of transmission to less than 1% of total spectral power. In some embodiments, the notch filter 120 attenuates a filtered range of transmission to less than 0.1% of total spectral power. In some embodiments, the notch filter 120 attenuates a filtered range of transmission which may incorporate a portion of one or several of the ranges described above.

In some embodiments the filtered range of transmission can include a cutoff of any light below one of the following wavelengths: 420 nm, 430 nm, 440 nm, 450 nm, 460 nm, 470 nm, 480 nm, 490 nm, 500 nm, 510 nm, 520 nm. In some embodiments, the filtered range of transmission can include any one of the following ranges: between about 420 nm and 490 nm; between about 430 nm and 490 nm; between about 440 nm and 490 nm; between about 450 nm and 490 nm; between about 460 nm and 490 nm; between about 420 nm and 480 nm; between about 430 nm and 480 nm; between about 440 nm and 480 nm; between about 450 nm and 480 nm; between about 460 nm and 480 nm; between about 420 nm and 470 nm; between about 430 nm and 470 nm; between about 440 nm and 470 nm; between about 450 nm and 470 nm; between about 420 nm and 460 nm; and between about 440 nm and 460 nm. In some embodiments, the filtered range of transmission can be between 460-480 nm. In some embodiments, the filtered range of transmission can be between 430-490 nm. In other embodiments, the filtered range of transmission can include other ranges based on desired lighting conditions. In some embodiments, the notch filter 120 can create sharp transitions on either side of the absorption notch and high optical density inside the notch. The accuracy of the notch filter 120 allows the LED lighting system 100 to substantially block the small band of light with negative implications while producing illumination which is substantially similar to that of current lighting systems.

Different LEDs, depending on their design and power source, can provide varying levels of intensity of light at different wavelengths. Conventional LEDs incorporate a pump which increases the intensity of light at a LED in the approximate range of 440 nm and 470 nm. Testing has shown that the intensity spike at around 440 nm in a conventional LED is highly suppressive of melatonin. Testing has also shown that when a notch filter is utilized to attenuate the specific band implicated in circadian disruption, a conventional LED may not offer white light similar to that of unfiltered light. Under some circumstances a conventional LED with a notch filter will give a yellow hue which may not be conducive to an efficient working environment in some applications. In some embodiments, the LED lighting system incorporates LEDs 114 which incorporates a pump which increases the intensity of light in the approximate range of 400-420 nm as opposed to the conventional spike in the approximate range of 440 nm and 470 nm. In some embodiments, the LED lighting system incorporates LEDs 114 which incorporate a pump which increases the intensity of light in the approximate range of 380 and 430 nm as opposed to the conventional spike in the approximate range of wavelength between approximately 440 nm and 470 nm. In some embodiments, the LED lighting system incorporates LEDs 114 which incorporate a pump which increases the intensity of light at approximately 415 nm. Testing has shown that when a notch filter is utilized to attenuate the specific band implicated in circadian disruption, the LEDs with the 415 nm pump unexpectedly produces light substantially similar to unfiltered light. This improved filtered light can provide substantive attenuation of the pathologic circadian disruption in night workers while providing a quality light source to keep them alert, productive, and safe in the workplace. The improved filter light can offer increased alertness, increased vigilance, improved cognitive performance, and reduced accidents and injuries.

LEDs are a special type of diode which passes electric current in one direction only. LEDs convert the energy dissipated by the current passing through the diode into light. The color of light emitted is determined by the type of semiconductor material that is used in the active region of the device, and by the thickness of the individual layers within the active region. In some embodiments, LEDs use Gallium Nitride ("GaN") to produce a white light. The forward voltage drop (measured in volts) and the current through the diode, (measured in amps or miliamps) measure the wattage of the diode. In some embodiments, these are regulated by a drive, an electronic circuit between the LED and main power that maintains stable voltage and current in order to prevent the LED from fluctuating or burning up.

In one embodiment, high-intensity white light is produced using individual LEDs that emit three primary colors, red, green, and blue ("RGB"), and then mix all the colors to form white light. In other embodiments, high-intensity white light is produced by coating a GaN LED with a phosphor material to convert the typically blue monochromatic GaN emitted light into broad-spectrum white light. In some embodiments, GaN phosphor white offers much better color rendering that RGB white, often on a par with florescent sources. GaN phosphor white light can also be much more efficient than RGB white.

In some embodiments, GaN LEDs can be designed to emit any color in the range of UV-A (380 nm) to green (550 nm) by alloying the Gallium Nitride with Aluminum and/or Indium. In some embodiments, "white" LEDs use a GaN LED emitting blue light in the 440 nm-470 nm range which is covered by a yellowish phosphor coating which distributes the light wavelengths in the broad color spectrum necessary to provide white light. In some embodiments, a method of making a GaN LED includes crystal layers of GaN grown on a substrate material, which may include for example sapphire or silicon carbide. Due to differences in material properties between GaN and the substrate materials, the GaN crystal can grow imperfectly on the substrates and can produce a high incidence of imperfections which reduce the light generation efficiency of the LED. This loss of efficiency can be referred to as "droop" when the LEDs are driven with increasing electric current. Conventional approaches to high efficiency high intensity light production by LEDs tends to focus on GaN based LEDs emitting a spike of blue light in the 440-470 nm range.

In some embodiments, the light spectrum of these commonly available LEDs falls in the visual spectrum range that causes maximum stimulation of the melanopsin retinal ganglion cell receptors and the non-visual pathways controlling the circadian timing system and pineal. During night-time hours these LED based luminaires can cause suppression of melatonin with its attendant neuroendocrine and health disruptive effects.

In some embodiments, LED lighting systems can include optical filters that exclude light wavelengths between 425 and 490 (or variants of this e.g. 430-480 etc. to be iteratively determined) and light sources that emit a high intensity light spike in the violet wavelengths between 400 and 420 nm, because the combination of these wavelengths (400-420 plus 500-750 nm) do not trigger the melanopsin system at night.

In some embodiments, LED lighting systems can include a light source that emits a high intensity light spike in the 400-420 nm range to compensate for the yellow color distortion produce by a filter excluding light in the 425-490 blue wavelengths. In some embodiments, LED lighting systems can include a light source that emits a high intensity light spike in the 380-430 nm violet range to compensate for the yellow color distortion produce by a filter excluding light in the 430-490 nm blue wavelengths. In some embodiments, the light source can be LED-based as that is the most efficient and lowest cost solution at this time, however other light sources could be utilized which offer a similar high intensity light spike. In some embodiments, the light source can include GaN LEDs.

In some embodiments, LED lighting systems can include LEDs with a light intensity spike in the 400-420 nm range can combine a LED chip emitting light at 405 nm with a coating of phosphors. In some embodiments, LED lighting systems can include LEDs with a high efficiency GaN LED with a light intensity spike in the 400-420 nm range by growing the chip on a much more expensive GaN substrate as compared of the sapphire substrates which are used for conventional LED chips which can offer reduced defect densities reducing droop and allowing very high current densities to achieve high intensity light output. By growing the GaN crystals on a GaN substrate, the crystals can grow more perfectly, and thus accommodate much higher power densities and allow the LED to emit more light from the same crystal area.

In some embodiments, the LED lighting system 100 can include means for switching between a night configuration and a day configuration. In some embodiments the LED lighting system 100 can include a plurality of LED lights 110 which incorporate a notch filter 120 as illustrated in FIG. 1A and FIG. 1B and a plurality of LED lights 110 which do not incorporate a filter as illustrated in FIG. 2. In some embodiments, the LED lighting system 100 can switch from the plurality of LED lights 110 with notch filters 120 during the night to the plurality of LED lights 110 without notch filters during the day. In another embodiment, the LED lighting system 100 can be installed in conjunction with an existing light system, allowing the system to switch between the existing unfiltered light source during the day to the filtered LED lighting system 100 during the night. The ability of the LED lighting system 100 to switch back and forth between filtered light and unfiltered light is ideal for facilities which share day shift workers and night shift workers as it can provide full spectrum light during daytime hours and filtered healthy light at night. In some embodiments, the LED lighting system 100 can incorporate the capability of software and control systems to provide intelligent and personalized dynamic control of the circadian timing of light. In some embodiments, the LED lighting system 100 can incorporate a simple timer to switch between filtered light and unfiltered light.

In another embodiment, the LED lighting system can include a means for applying the notch filter 120 to the plurality of LED lights 110 selectively, so that the plurality of LED lights 110 are only subject to the notch filter 120 during the night. In some embodiments, the selective application of the notch filter 120 can include a means for moving the notch filter 120 into or out of the beam of light produced by the LED lights 110. In another embodiment, the selective application of the notch filter 120 can include a means for activating or deactivating the filter properties of the notch filter 120 so that in an deactivated state, the notch filter 120 allows a full spectrum of light through the notch filter 120 but in an activated state, the notch filter 120 prevents at least a majority of a prescribed filtered range of light from passing through the notch filter 120. In one embodiment, in an activated state, the notch filter 120 can allow less than 1% of light within the prescribed filtered range from passing through the notch filter 120.

Figure 4:
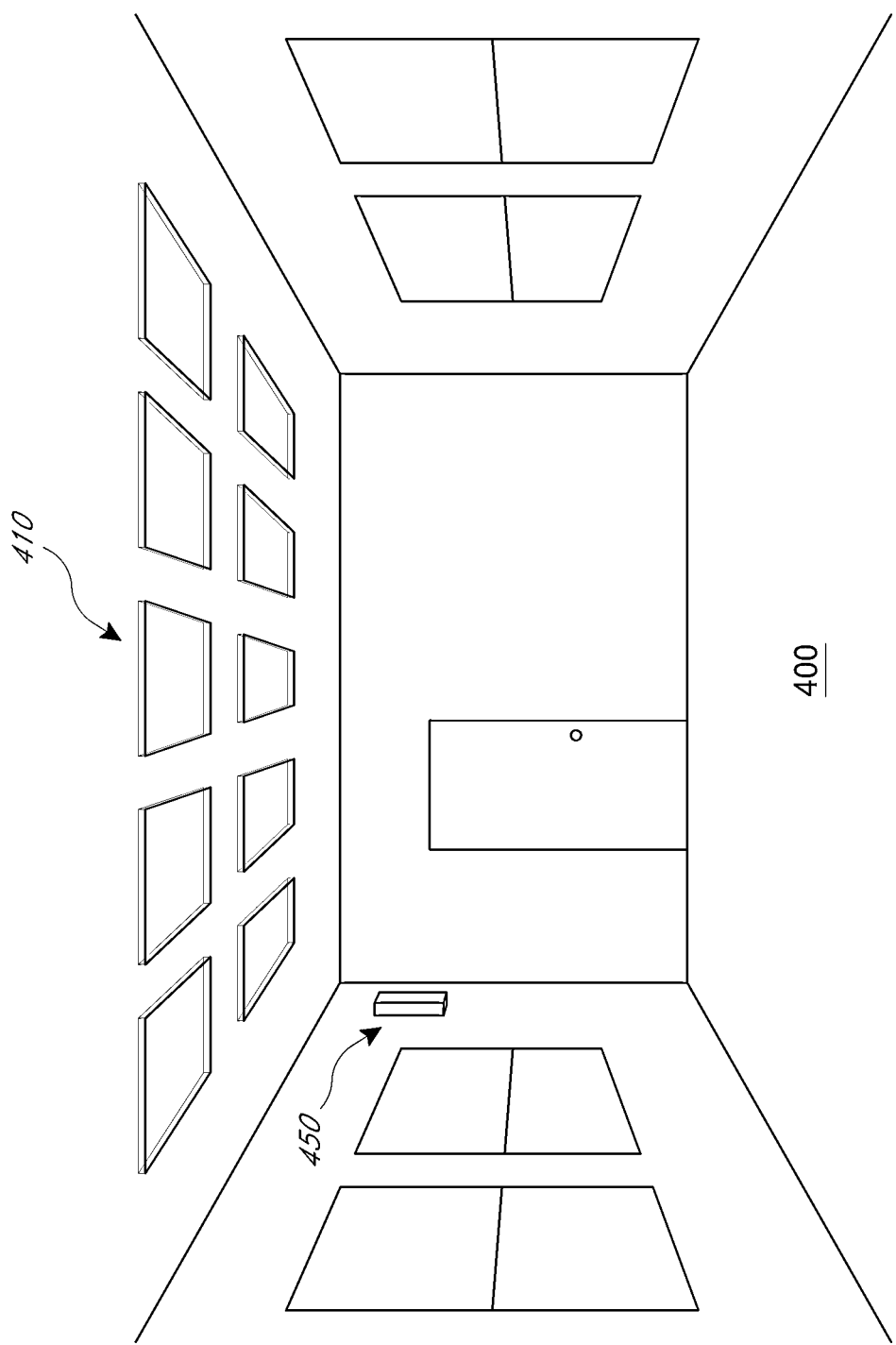
FIG. 4 illustrates one example of a workplace with a plurality of ceiling panels installed.

In some embodiments, an LED lighting system 100 incorporates a ceiling panel incorporating a plurality of LED lights 110. In some embodiments, the LED lighting system 100 is constructed for installation into standard lighting fixtures or existing receptacles for conventional panel lighting in industrial and commercial workplaces, minimizing the cost involved with converting existing workplaces and installing an LED lighting system 100. FIG. 4 illustrates one example of a workplace 400 with a plurality of ceiling panels 410 installed. In some embodiments, the ceiling panel 410 can be approximately 24" long by 24" wide. In some embodiments, the ceiling panel 410 can be approximately 48" long by 24" wide. In some embodiments, the ceiling panel 410 can be 48"×12" wide. In some embodiments, other sizes of ceiling panel 410 are possible. In some embodiments, the ceiling panel 410 can include 4 to 24 LED lights 110. In some embodiments, the ceiling panel 410 can include 12 LED lights 110. In some embodiments the operating voltage of the LED lighting system 100 can be approximately 90 to 277 Volts AC at approximately 50/60 Hertz. In some embodiments, the ceiling panel 410 can be constructed of steel or aluminum. In some embodiments the LED lights 110 can comprise MR16 bulbs, such as, for example, those commercially available from Soraa, Inc. of Fremont, CA In other embodiments, the LED lights 110 can include an LED chip array. In other embodiments, the LED lights 110 can include an LED chip array including GaN on GaN chips such as, for example, those commercially available from Soraa, Inc. of Fremont, CA In some embodiments, the LED lighting system can include a gateway 450 or controller.

Figure 5A:
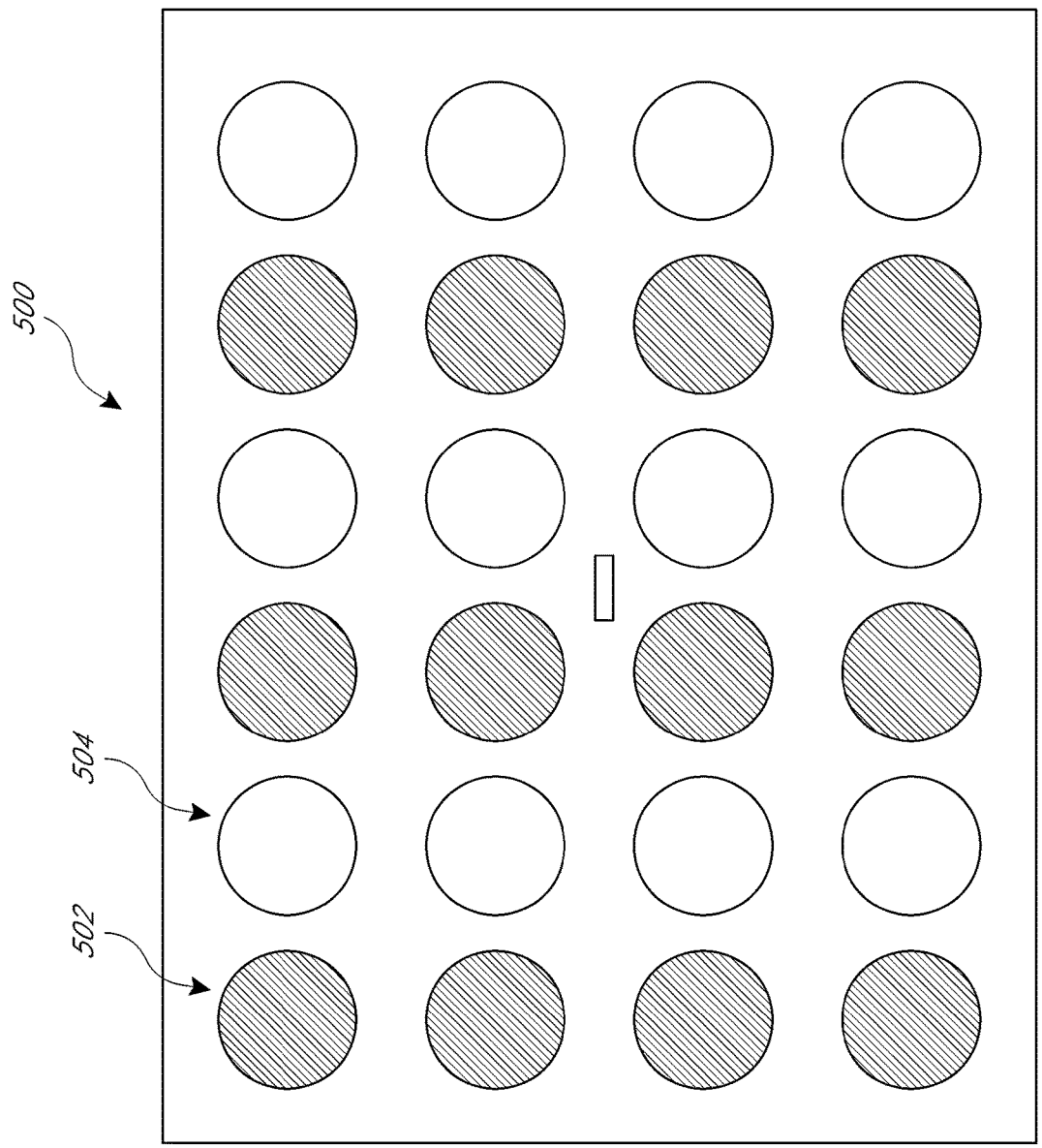
FIG. 5A illustrates a bottom view of one embodiment of a filter plate.
Figure 5B:
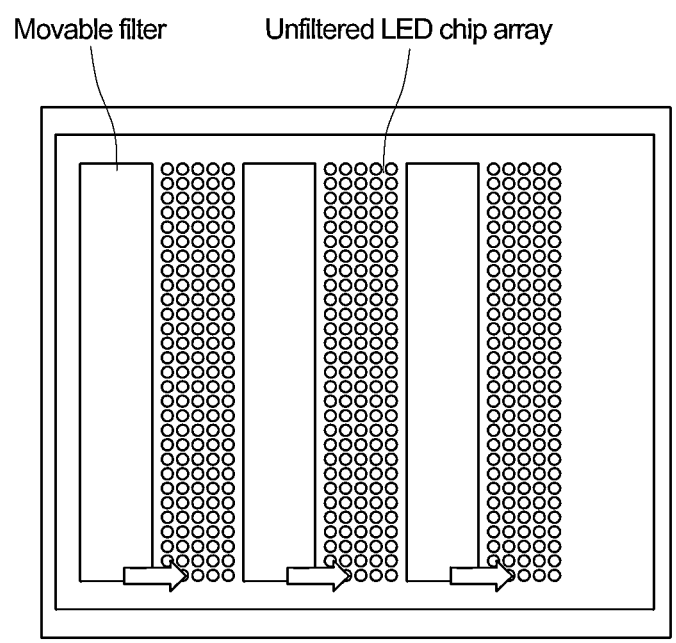
FIG. 5B illustrates a bottom view of one embodiment of LED chip arrays with movable filters.

FIG. 5A illustrates a bottom view of one embodiment of a filter plate. FIG. 5B illustrates a bottom view of one embodiment of LED chip arrays with movable filters. In some embodiments, the LED lighting system 100 can include a filter plate 500 capable of selectively filtering the light produced by the LED lighting system 100. In some embodiments, the filter plate 500 incorporates at least one filtered portion 502 and at least one unfiltered portion 504. In some embodiments, the filtered portion 502 can include a plurality of apertures which include a filter, which may include for example any of the filters described herein. In some embodiments, the unfiltered portion 503 can include a plurality of apertures which do not include a filter. In some embodiments, the filter plate 500 can include a plurality of filtered portions 502 and unfiltered portions 504. In some embodiments, filtered portions 502 and unfiltered portions 504 are oriented on the filter plate 500 such that movement of the plate changes the portion of the plate through which light passes through, which may include light produced by one of the LED lights described herein. The light can pass through either the filtered portions 502 of the filter plate 500 or through the unfiltered portions 504 of the filter plate 500. In some embodiments, the filter plate 500 is constructed to slide so that light may be directed through the unfiltered portions 504 during the day and through the filtered portions 502 during the night.

Figure 6B:
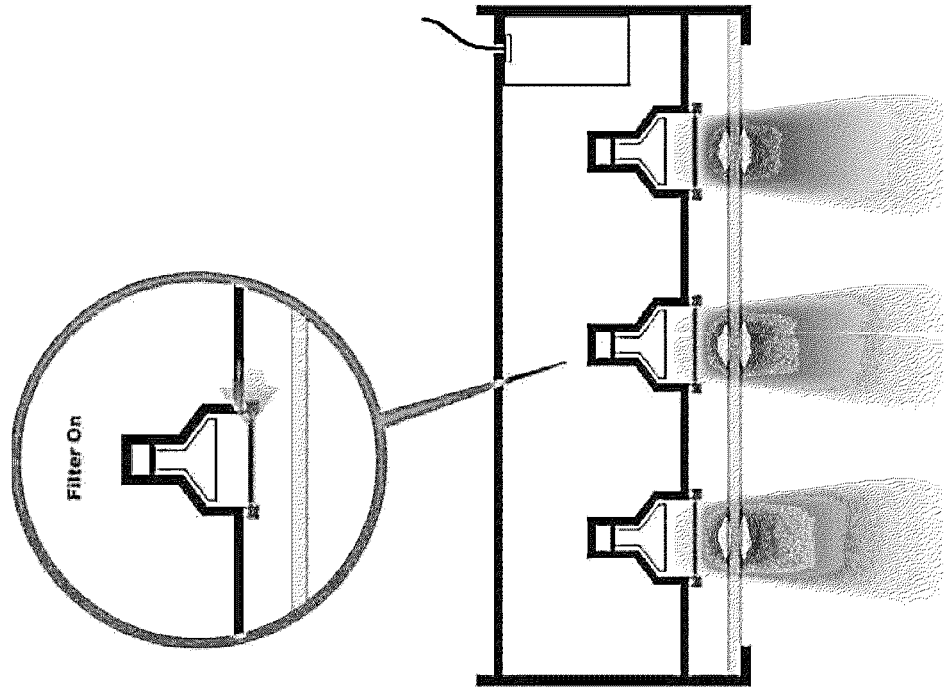
FIG. 6B illustrates a side view of one embodiment of a LED lighting system including MR16 LEDs in a filtered position.
Figure 6A:
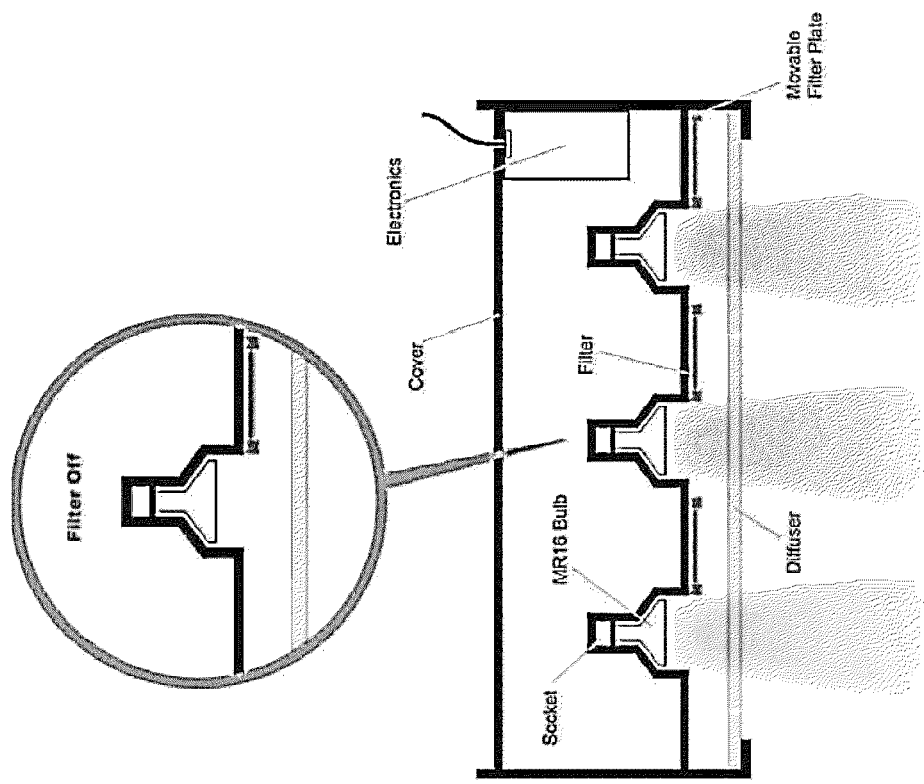
FIG. 6A illustrates a side view of one embodiment of a LED lighting system including MR16 LEDs in an unfiltered position.

FIG. 6A illustrates a side view of one embodiment of a LED lighting system including MR16 LEDs in an unfiltered position. FIG. 6B illustrates a side view of one embodiment of a LED lighting system including MR16 LEDs in a filtered position. FIG. 6C illustrates a side view of one embodiment of a LED lighting system including LED arrays in an unfiltered position. FIG. 6D illustrates a side view of one embodiment of a LED lighting system including LED arrays in a filtered position. In some embodiments, the filters may be housed in a filter plate 500 as described above. In some embodiments, the filters may move side to side individually or in rows. In some embodiments, as illustrated in FIGS. 6A and 6C, the LED lighting system can be in a daytime configuration where the filters are not in the path of the light and do not attenuate any of the light. In some embodiments, as illustrated in FIGS. 6B and 6D, the LED lighting system can be in a night time configuration where the filters are in the path of the light and attenuate at least a portion of the light passing through them. In some embodiments, in a night time configuration, the LED lighting system would not allow a substantial amount of unfiltered light to pass into the workplace 400. In some embodiments, the filter plate incorporating the filtered portions 502 and the unfiltered portions 504 can move laterally in a direction substantially perpendicular to the light produced by the LED lighting system. In another embodiment, the filters could rotate between a filtered night time configuration and an unfiltered day time configuration. In some embodiments, movement of the filter plate or the filters is controlled by a servo. One skilled in the art will realize that light sources other than MR16 LEDs or LED arrays can be used with a moveable filter or filter plate.

Figure 7A:
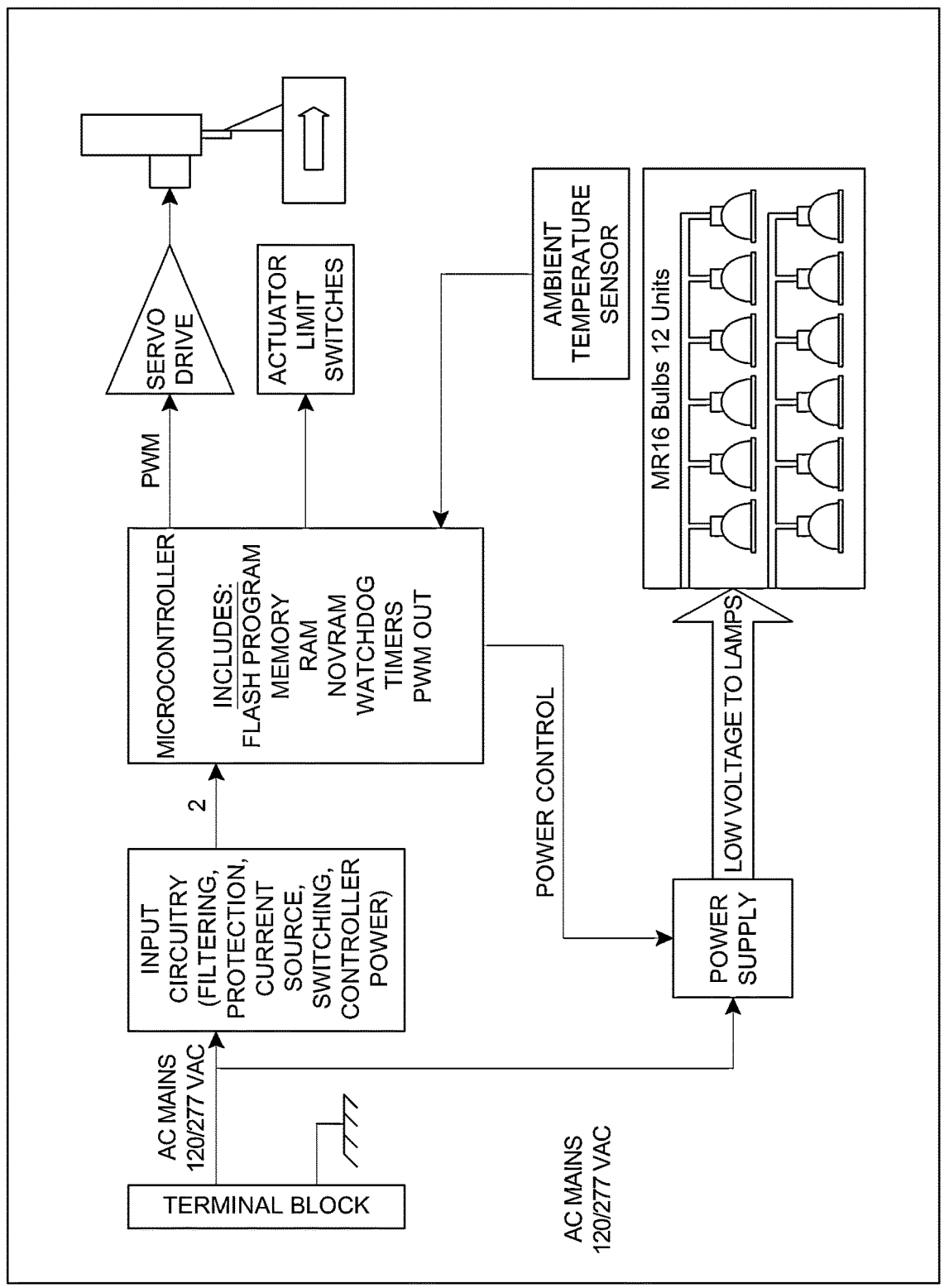
FIG. 7A illustrates an LED lighting system including MR16 LEDs and a control system.
Figure 7B:
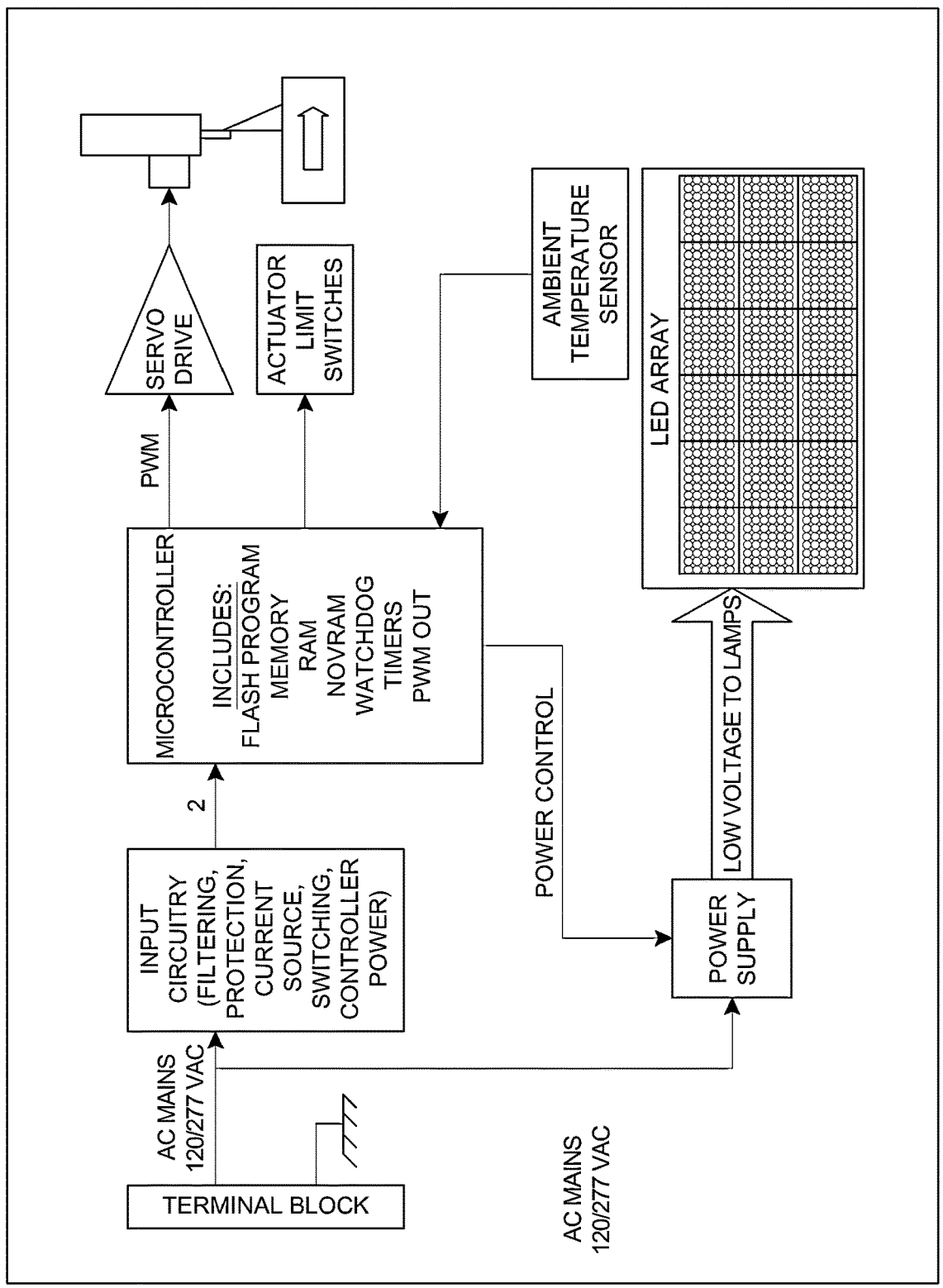
FIG. 7B illustrates an LED lighting system including LED chip arrays and a control system.

FIG. 7A illustrates an LED lighting system including MR16 LEDs and a control system. FIG. 7B illustrates an LED lighting system including LED chip arrays and a control system. In some embodiments the LED lighting system can include a control system. In some embodiments the LED lighting system can include a terminal block, a power supply, input circuitry, a micro controller, an ambient temperature sensor, a servo drive, a servo, and actuator limit switches. In some embodiments the control system, based on any number of inputs which may include the time of day, can control whether the LED lighting system is in an unfiltered day time configuration or in a filtered night time configuration. In some embodiment, the control system can activate a servo to change the LED lighting system from an unfiltered day time configuration or in a filtered night time configuration. In some embodiments, the LED lighting system can include actuator limit switches so that the control system knows when the LED lighting system has reached the proper orientation to be in a filtered or an unfiltered state, and can use that data to ensure the LED lighting system is in the proper configuration. In some embodiments, an electrical actuator can be used for filter positioning.

In some embodiments, the LED lighting system can be remote controlled from an in-room gateway 450 as illustrated in FIG. 4 through power-line communications. In some embodiments, control of the LED lighting system can use X-10 or Insteon standards. In some embodiments, the control system can control both the brightness of the LED lighting system as well as the filtered or unfiltered configuration of the LED lighting system. In some embodiments, the control system can ensure that all of the LED lights in the LED lighting system are adjusted substantially in unison and in substantially the same sequence.

Testing and Validation

As mentioned above, testing has shown that the intensity spike at around 440 nm in a conventional LED is highly suppressive of melatonin. Testing has also shown that when a notch filter is utilized to attenuate the specific band implicated in circadian disruption, a conventional LED may not offer white light similar to that of unfiltered light. Two types of LED lights were utilized in testing, one including a 440 nm pump and one including a 415 nm pump.

Figure 8:
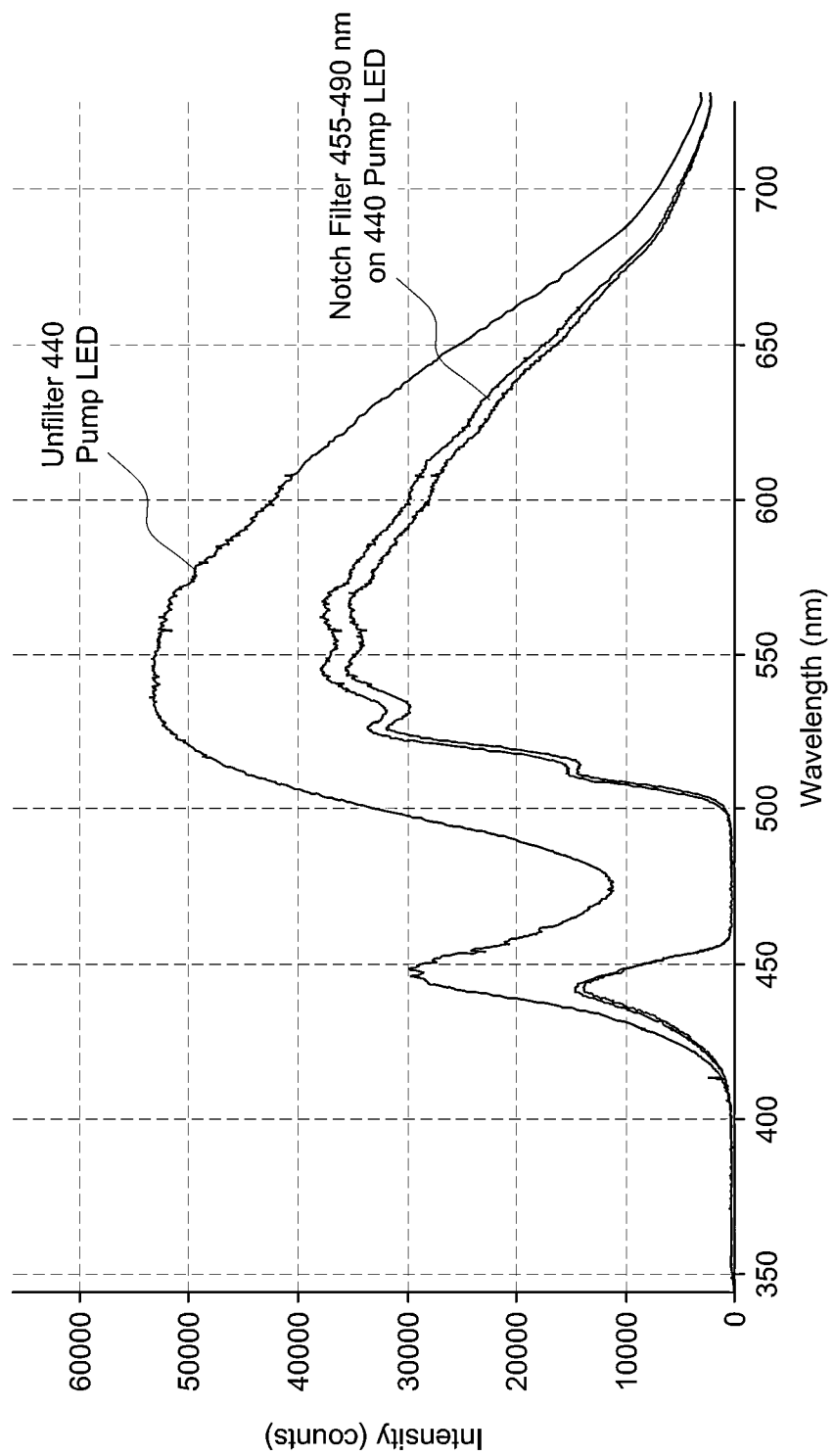
FIG. 8 illustrates the intensity of light across the visual spectrum produced by an approximately 440 nm pump LED, both filtered and unfiltered.

FIG. 8 illustrates the intensity of light across the visual spectrum produced by an approximately 440 nm pump LED, both filtered and unfiltered. The filtered spectrum includes a filtered range between 455-490 nm. Testing has shown that the 455-490 nm notch filter in combination with the 440 nm pump LED is ineffective at restoring melatonin to desired levels. Further testing showed that a cut-off filter below 500 nm on a 440 nm pump LED is effective at restoring melatonin to desired levels, however the resulting filtered light was unacceptable for some applications as it offered a yellow hue versus the desired white light. In some other applications, a cut-off filter and/or light with a yellow hue may provide an acceptable environment of filtered light if desired.

Figure 9:
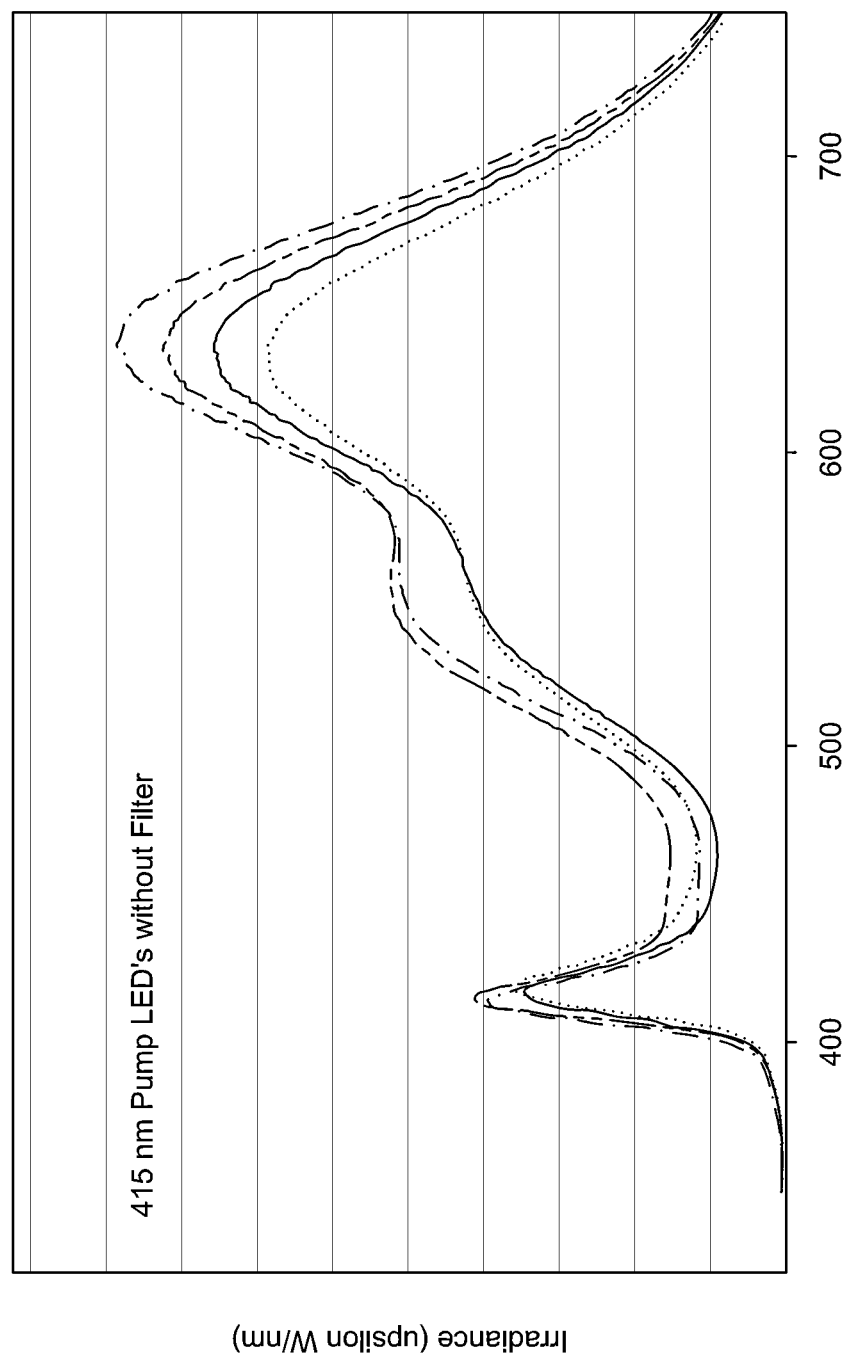
FIG. 9 illustrates the relative intensity of light along the spectrum produced by a several color temperature varieties of an approximately 415 nm pump LEDs.
Figure 10:
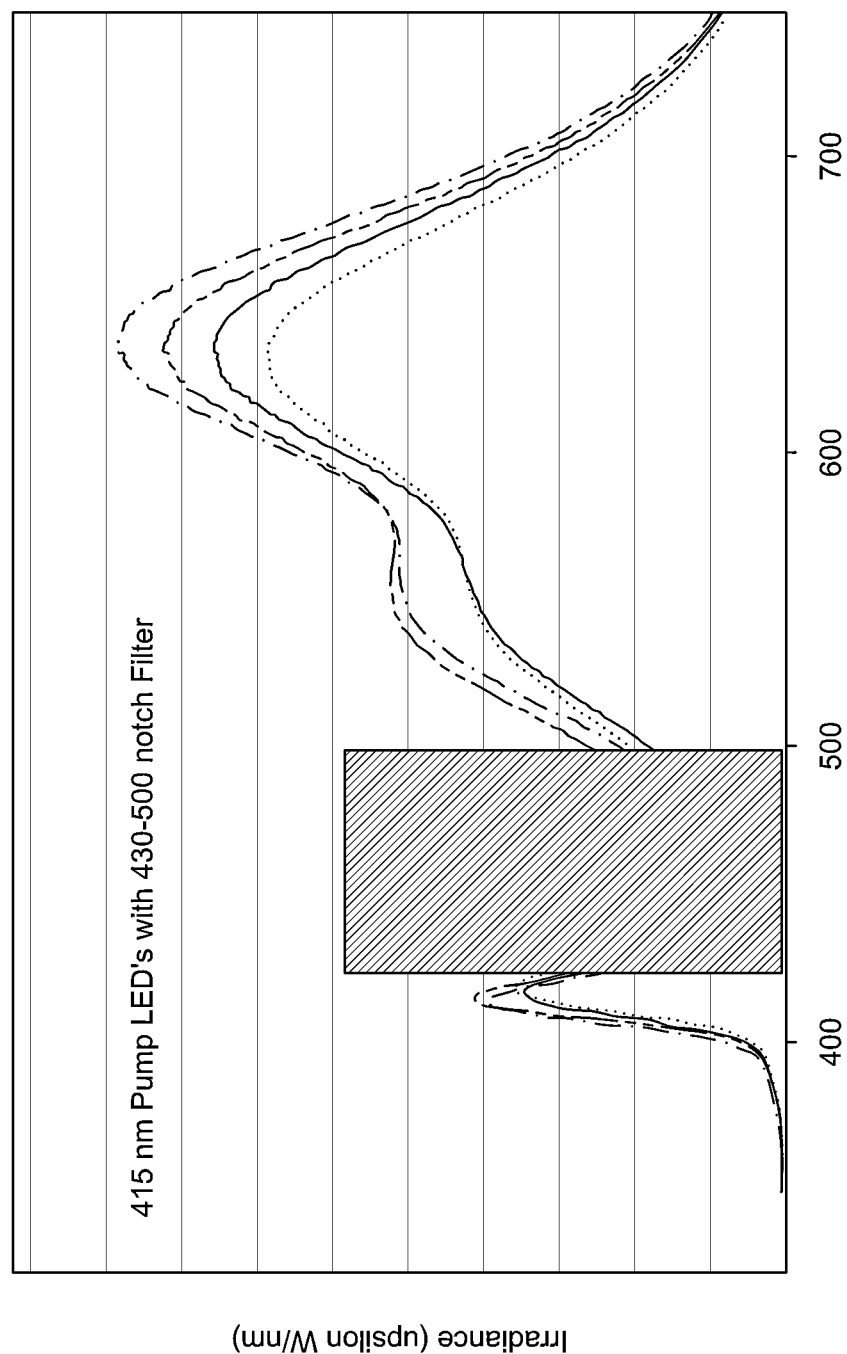
FIG. 10 illustrates the relative intensity of light along the spectrum produced by a variety of an approximately 415 nm pump LED including a 430-500 nm notch filter.

FIG. 9 illustrates the relative intensity of light along the spectrum produced by a several color temperature varieties of an approximately 415 nm pump LEDs. FIG. 10 illustrates the relative intensity of light along the spectrum produced by a variety of an approximately 415 nm pump LED including a 430-500 nm notch filter. Testing has shown that the 430-500 nm notch filter in combination with the 415 nm pump LED is effective at restoring melatonin to desired levels as well as creating the desired white light.

Figure 11A:
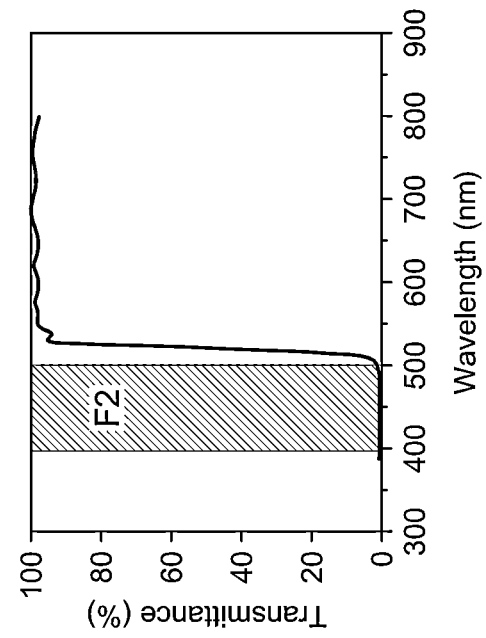
FIG. 11A represents the light transmittance percentage for a 455-490 nm notch filter on a LED with a 440 nm pump.
Figure 11B:
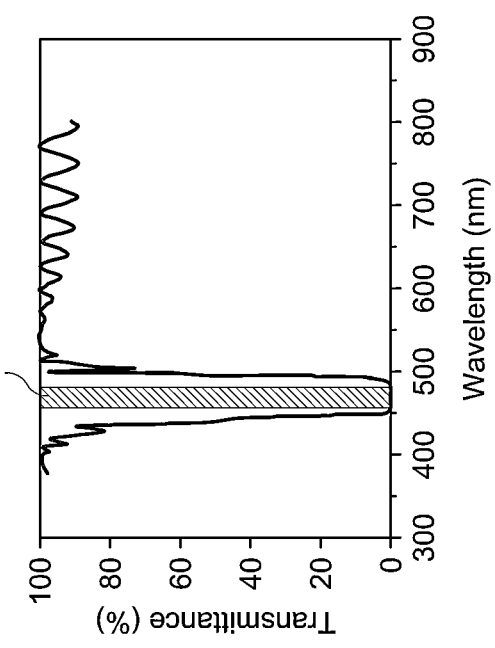
FIG. 11B represents the light transmittance percentage for a sub 500 nm cut off filter on an LED with a 440 nm pump.
Figure 11C:
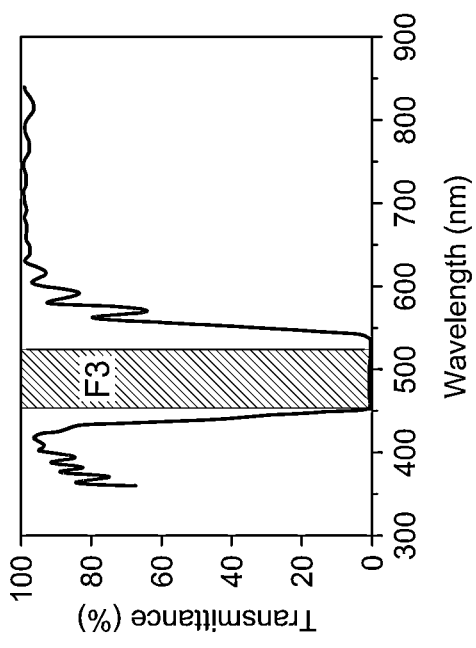
FIG. 11C represents the light transmittance percentage for a 430-500 nm notch filter on a LED with a 415 nm pump.

Several custom filters were manufactured for the testing process. FIG. 11A represents the light transmittance percentage for a 455-490 nm notch filter on a LED with a 440 nm pump. FIG. 11B represents the light transmittance percentage for a sub 500 nm cut off filter on an LED with a 440 nm pump. FIG. 11C represents the light transmittance percentage for a 430-500 nm notch filter on a LED with a 415 nm pump. The shaded area in FIGS. 11A-C represents the wavelength range for which less than 1% transmittance was designed, and all three filters fulfilled the designed less than 1% transmittance requirement.

Figure 12A:
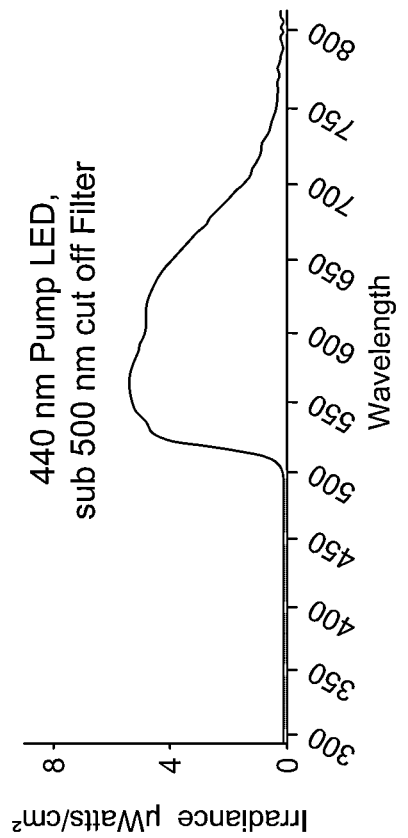
FIG. 12A represents the spectrometer measurements for an approximately 440 nm pump LED fitted with a 455-490 nm notch filter.
Figure 12B:
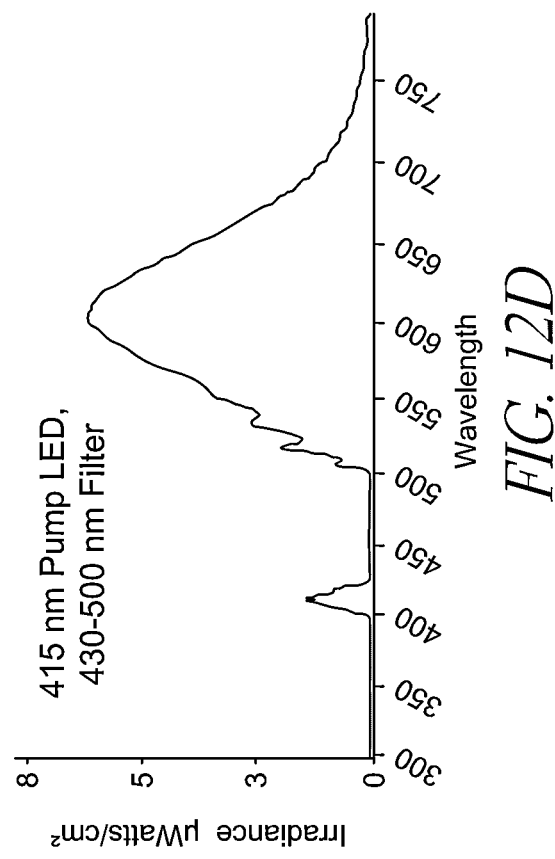
FIG. 12B represents the spectrometer measurements for an approximately 440 nm pump LED fitted with a sub 500 nm cut off filter.
Figure 12C:
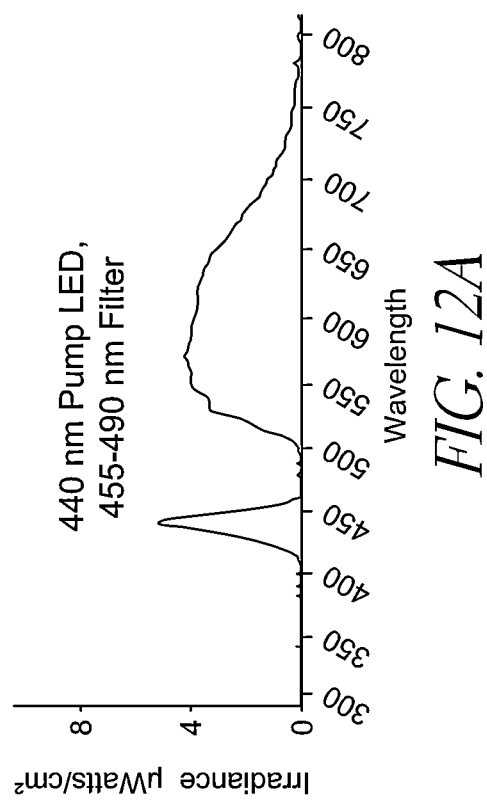
FIG. 12C represents the spectrometer measurements for an approximately 415 nm pump LED without a filter.
Figure 12D:
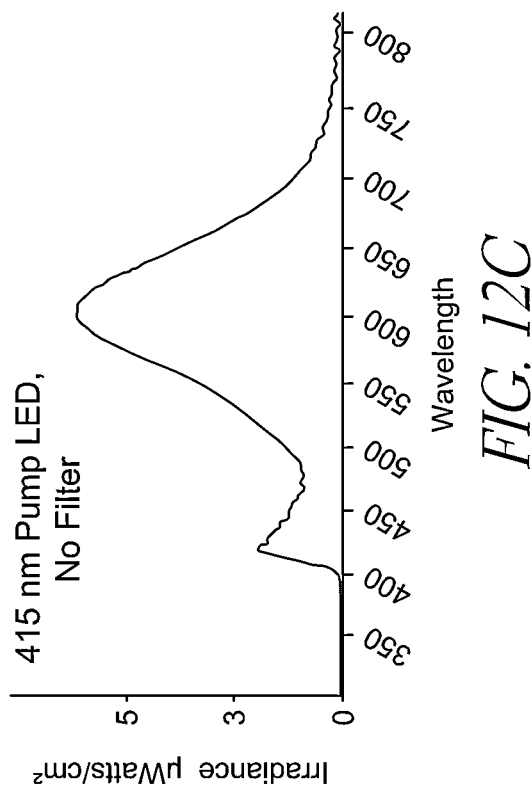
FIG. 12D represents the spectrometer measurements for an approximately 415 nm pump LED with a 430-500 nm notch filter.

Several prototype LED lighting systems were produced for the testing process utilizing the custom filters described above. FIG. 12A represents the spectrometer measurements for an approximately 440 nm pump LED fitted with a 455-490 nm notch filter. FIG. 12B represents the spectrometer measurements for an approximately 440 nm pump LED fitted with a sub 500 nm cut off filter. FIG. 12C represents the spectrometer measurements for an approximately 415 nm pump LED without a filter. FIG. 12D represents the spectrometer measurements for an approximately 415 nm pump LED with a 430-500 nm notch filter.

Twelve healthy individuals were enrolled in an overnight study. The group included five females and seven males.

Ages ranged from 22-34 years of age, with the mean age being 26.5 years. Exclusion criteria included recent history of shiftwork, sleep disorders, ocular/vision disorders, color blindness, a score greater than 16 on the Centre for Epidemiologic Studies Depression Scale, suggestions of depression, being on medication, smoking, irregular habitual sleep pattern with bedtimes and wake-up times deviating by 2+ hours from 2300 and 0700, respectively. All female participants were on oral contraceptives to prevent hormonal variability that could affect melatonin secretion. As part of the screening process, subjects provided saliva samples for melatonin analysis which they collected at home at the midpoint of their nocturnal sleep while in a dim/dark room. This sampling time coincides with the time when melatonin typically peaks, and only participants who had medium/high melatonin levels were enrolled for the overnight studies (low secretors did not qualify for the study as no strong differences in melatonin production between different lighting conditions were expected). Prior to the test nights, subjects participated in training sessions to practice the performance tests. They were asked to keep their regular sleep schedule during the week prior to each test night with bedtimes and wake-up times not deviating by more than 1 hour from 2300 and 0700, respectively (verified by sleep diaries and activity monitor recordings).

The study design was a within-subject design allowing direct individual comparisons with subsets of the participant group for added pilot studies with modified light filters testing. All twelve subjects completed testing of the light from 440 nm pump LEDs without a filter as well as light from the 440 nm pump LEDs with a 455-490 nm notch filter. Groups of four subjects participated in additional pilot testing with light from 440 nm pump LEDs with a sub 500 nm cut off filter and light from the 415 nm pump LEDs with a 430-500 nm notch filter.

The overnight protocol included hourly saliva sampling from 2000 to 0800. Double samples of saliva were analyzed for melatonin. Every two hours the following tests were performed: neuropsychometric subjective tests on mood using the visual analog scale, sleepiness using the Stanford Sleepiness Scale, fatigue using the Samn-Perelli Scale, alertness using the Toronto Hospital Alertness Test, and a 2-min cognitive performance test. Every four hours vigilance was measured objectively using the Digit Vigilance Test. Subjects completed a lighting assessment survey at midnight and at the end of each test night. Subjects were studied in groups of four, and were playing board games between test sessions. No sleep was allowed. Isocaloric snacks were served every four hours after saliva sampling, and subjects rinsed their mouth after eating. No food or water was allowed during 25 min prior to saliva sampling.

The different lighting conditions were provided in form of ceiling lighting. Light intensity at the angle of gaze was about 300-400 lux. After arrival at the laboratory at 18:15, subjects were exposed to standard fluorescent office ceiling lighting until they had completed the first test session at approximately 2000.

Figure 13A:
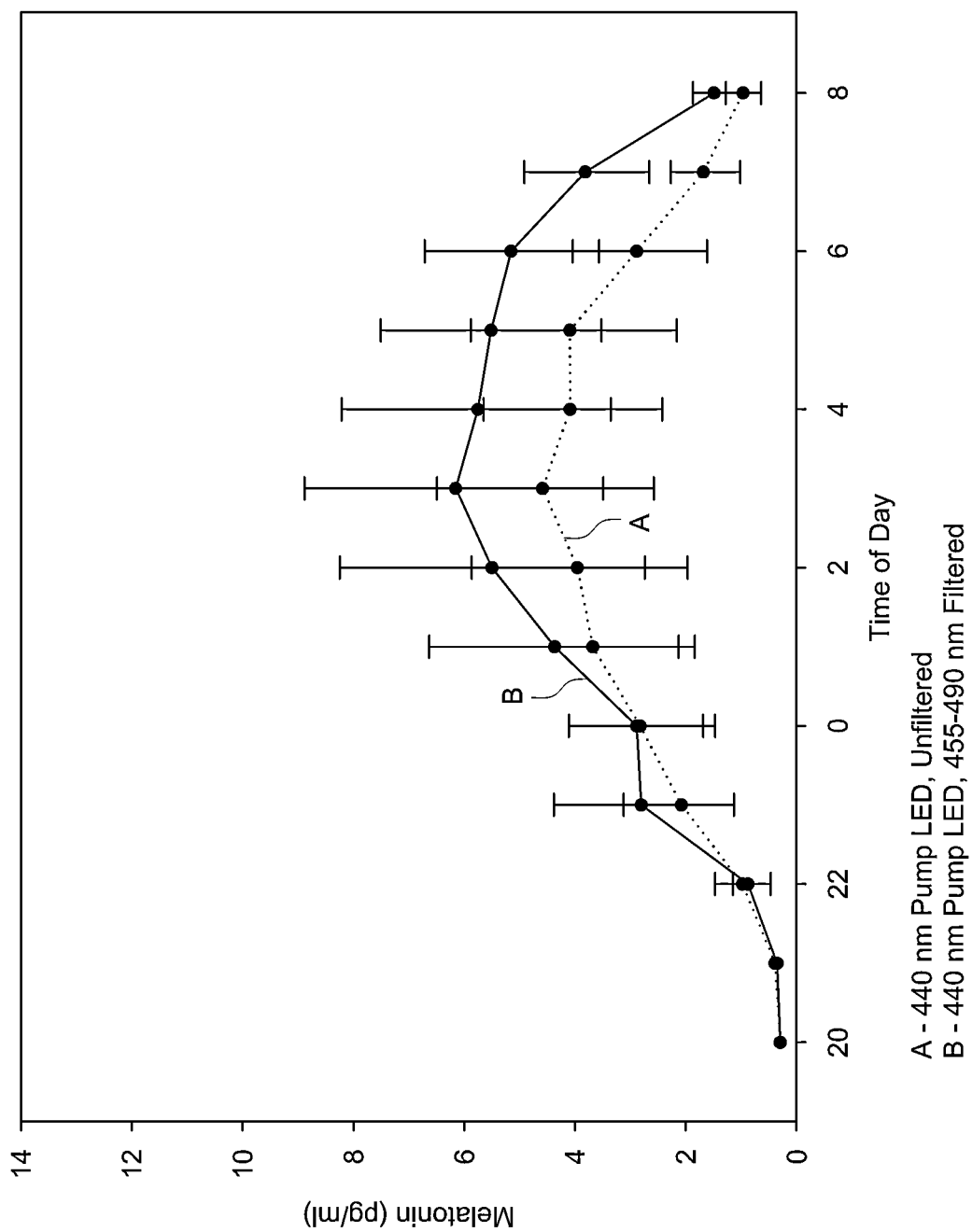
FIG. 13A illustrates the melatonin levels for twelve subjects exposed to 455-490 nm filtered and unfiltered light produced by an approximately 440 nm pump LEDs.
Figure 13B:
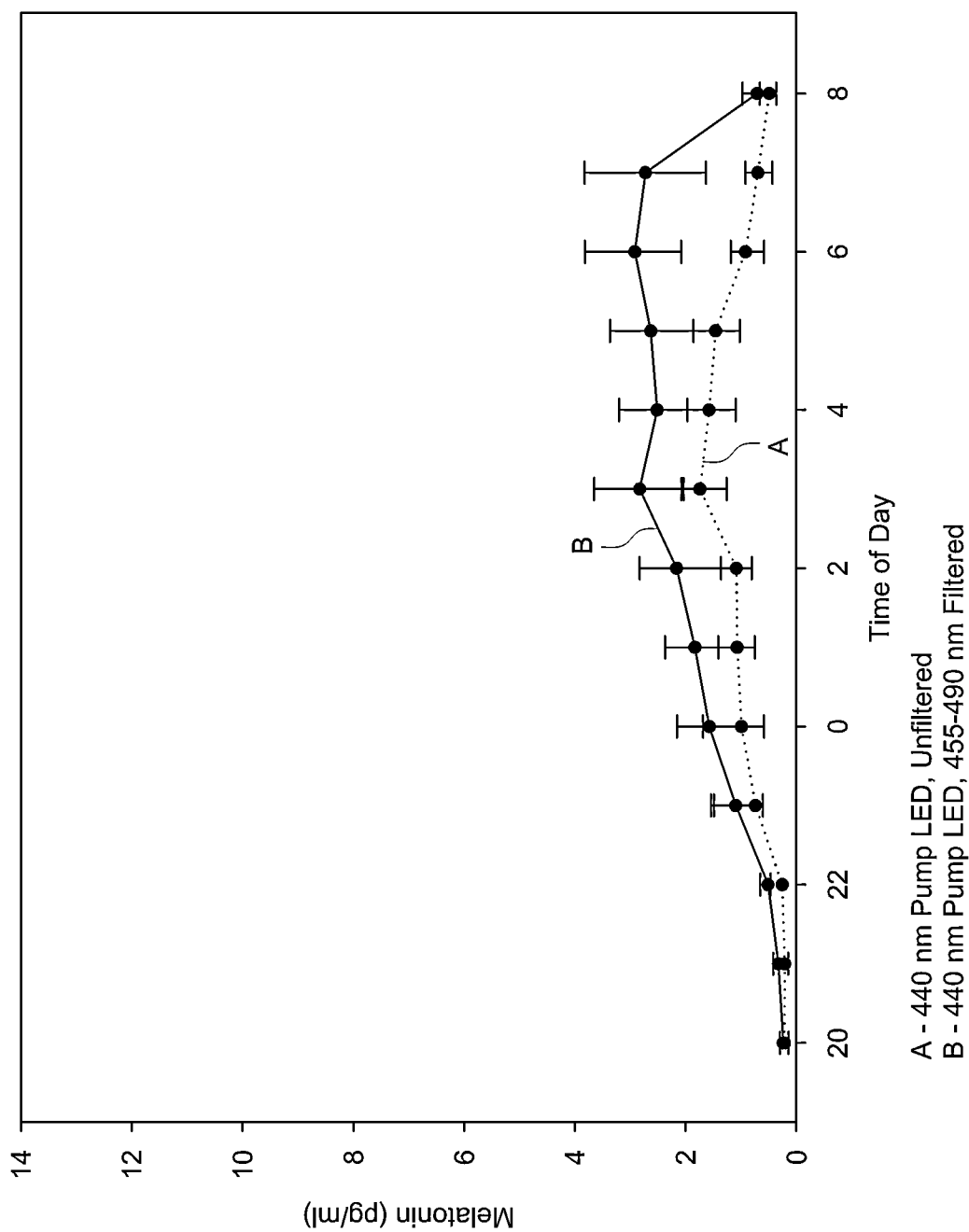
FIG. 13B illustrates the melatonin levels for nine subjects exposed to 455-490 nm filtered and unfiltered light produced by approximately 440 nm pump LEDs.
Figure 14:
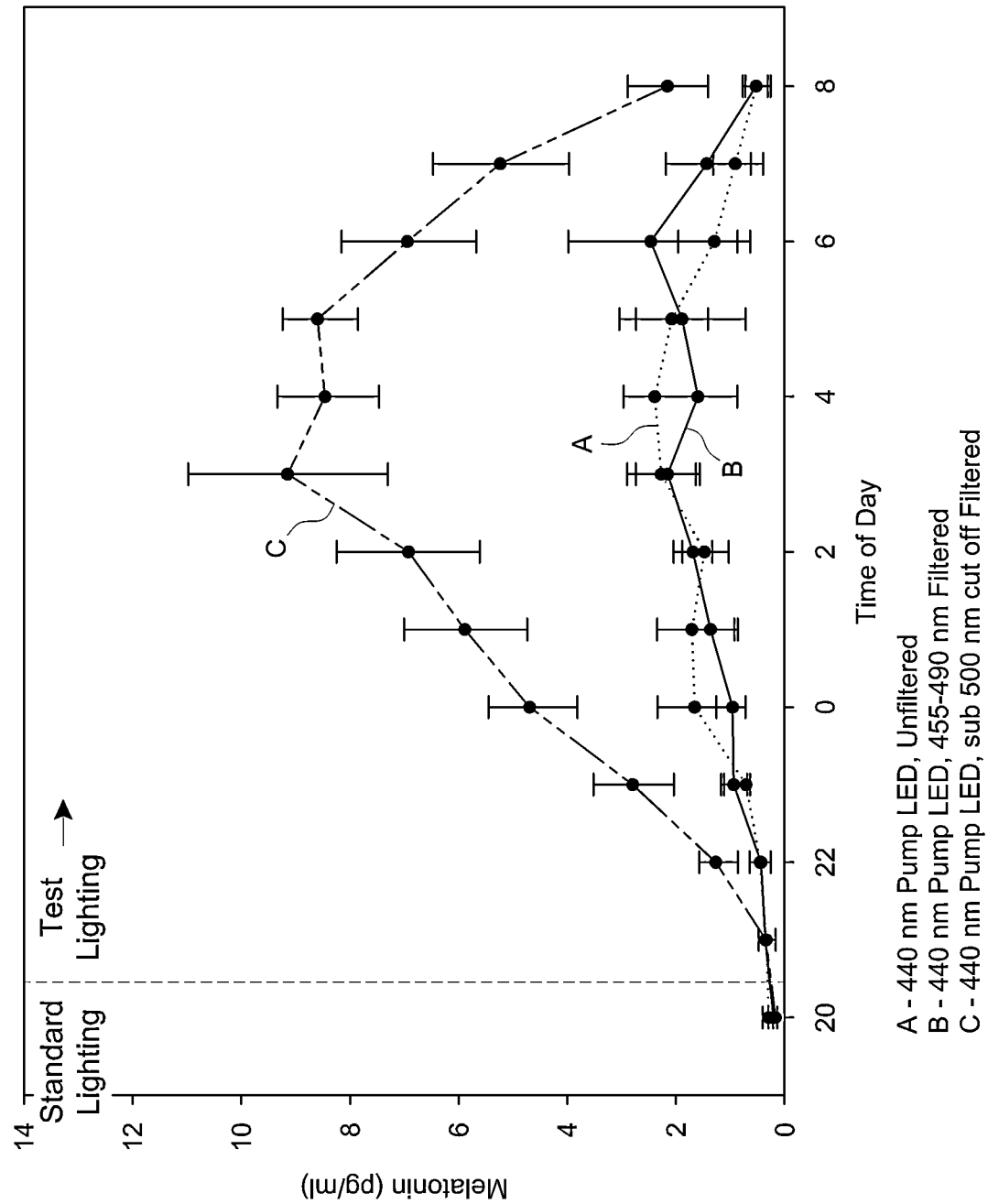
FIG. 14 illustrates the melatonin levels for four subjects exposed to filtered and unfiltered light produced by approximately 440 nm pump LEDs.
Figure 15:
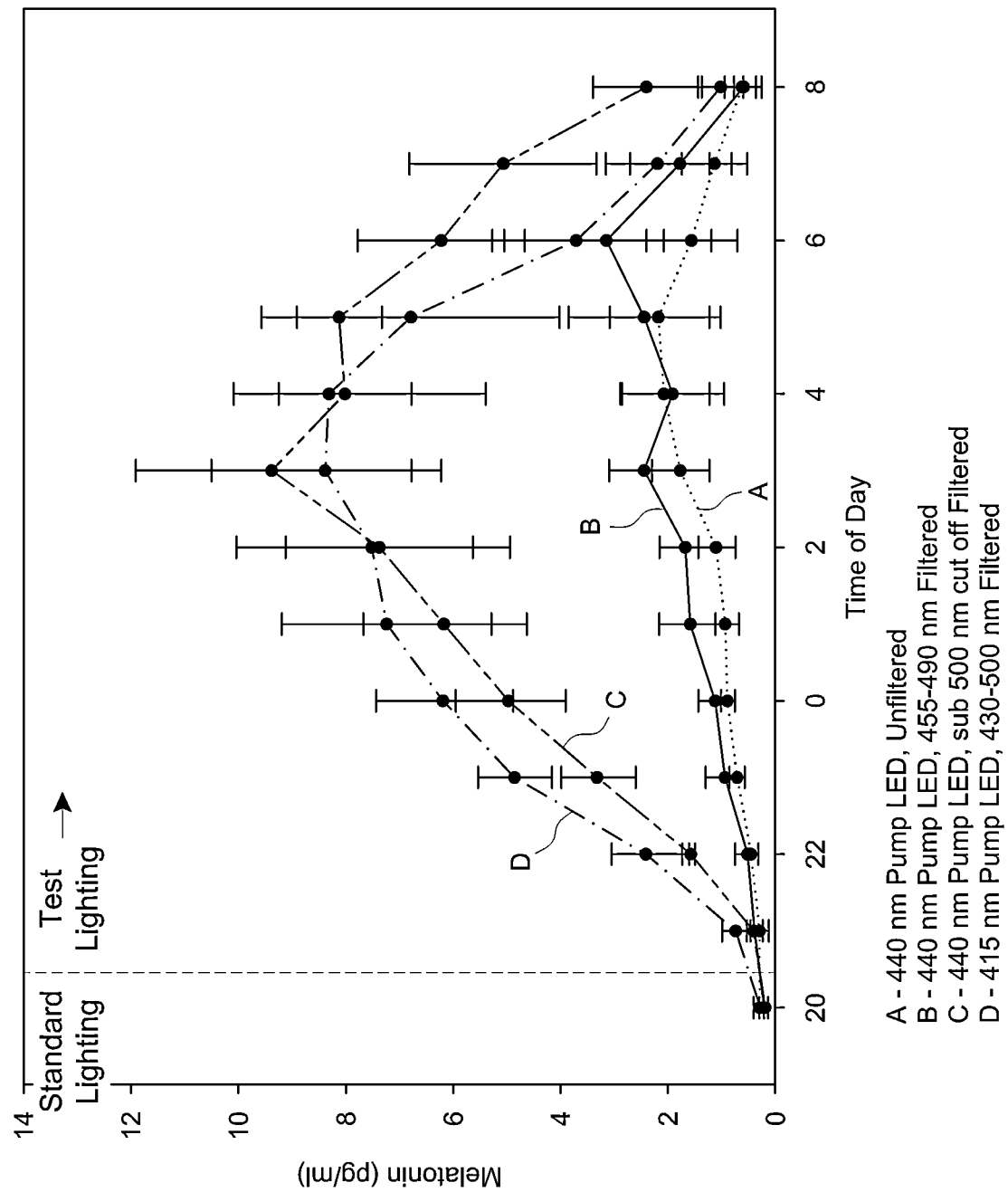
FIG. 15 illustrates the melatonin levels for four subjects exposed to filtered and unfiltered light produced by approximately 440 nm pump LEDs and filtered light produced by approximately 415 nm pump LEDs.

FIGS. 13-15 illustrate average melatonin levels in subjects over time when subjected to various LED and filter combinations. FIG. 13A illustrates the melatonin levels for twelve subjects exposed to 455-490 nm filtered and unfiltered light produced by an approximately 440 nm pump LEDs. The A line represents the average melatonin levels in subjects overnight when exposed to light from 440 nm pump LEDs without a filter. The B line represents the average melatonin levels in subjects overnight when exposed to light from 440 nm pump LEDs with a 455-490 nm notch filter.

Statistically significant differences between the two lighting conditions were found for the early morning hours, however the magnitude of the melatonin difference was relatively small. Low melatonin levels are typically expected when exposed to unfiltered light at night, and this was seen in most subjects. Subjects with increased baseline melatonin levels with the unfiltered light condition, which could be due to their individual-specific different reactions to the specific spectral composition of LED lighting, and one subject with poor saliva production ability, which led to exceedingly high melatonin baseline levels due to extremely long sampling times necessary to achieve the required saliva volume, were excluded from the subsequent melatonin analysis illustrated by FIG. 13B. FIG. 13B illustrates the melatonin levels for nine subjects exposed to 455-490 nm filtered and unfiltered light produced by approximately 440 nm pump LEDs. FIG. 13B excludes the outliers of FIG. 13A as described above. As in FIG. 13A, the A line represents the average melatonin levels in subjects overnight when exposed to light from 440 nm pump LEDs without a filter. The B line represents the average melatonin levels in subjects overnight when exposed to light from 440 nm pump LEDs with a 455-490 nm notch filter.

Four of the remaining subjects participated additional pilot testing as illustrated in FIG. 14 which included an additional 440 nm LED light source with a sub 500 nm cut off filter and three of them were able to participate in a fourth overnight study as illustrated in FIG. 15 which included 415 nm LED light with a 430-500 nm notch filter. FIG. 14 illustrates the melatonin levels for four subjects exposed to filtered and unfiltered light produced by approximately 440 nm pump LEDs. The A line represents the average melatonin levels in subjects overnight when exposed to light from 440 nm pump LEDs without a filter. The B line represents the average melatonin levels in subjects overnight when exposed to light from 440 nm pump LEDs with a 455-490 nm notch filter. The C line represents the average melatonin levels in subjects overnight when exposed to light from 440 nm pump LEDs with a sub 500 nm cut off filter.

FIG. 15 illustrates the melatonin levels for four subjects exposed to filtered and unfiltered light produced by approximately 440 nm pump LEDs and filtered light produced by approximately 415 nm pump LEDs. The A line represents the average melatonin levels in subjects overnight when exposed to light from 440 nm pump LEDs without a filter. The B line represents the average melatonin levels in subjects overnight when exposed to light from 440 nm pump LEDs with a 455-490 nm notch filter. The C line represents the average melatonin levels in subjects overnight when exposed to light from 440 nm pump LEDs with a sub 500 nm cut off filter. The D line represents the average melatonin levels in subjects overnight when exposed to light from 415 nm pump LEDs with a 430-500 nm notch filter. The data illustrates that melatonin levels for the 440 nm pump LEDs with 455-490 nm notch Filter (Line B) are quite similar to the melatonin levels for the unfiltered 440 nm pump LEDs (Line D), a control value representing a full spectrum of light in conventional workplaces. which represents a control full spectrum of light. This shows that the conventional LED with increased intensity at approximately 440 nm along with the 455-490 nm notch filter is not effective at maintaining appropriate melatonin levels of the subjects during night time exposure. On the other hand, Line C, representing the 440 nm pump LEDs with a sub 500 nm cut off filter, and Line D, representing the 415 nm pump LEDs with a 430-500 nm notch filter, maintain desired levels of melatonin during night time exposure. The pilot testing clearly demonstrated that nocturnal light-induced melatonin suppression can be limited by spectrum-specific, filtered LED lighting, specifically by lighting produced by 415 nm pump LEDs with a 430-500 nm notch filter.

The testing also included subjective assessments of each light source to identify potential barriers to adoption. Subjects completed a light assessment survey in the middle and at the end of each night. Visual Analog Scales were used to assess: general illumination, brightness and light distribution in the room, light color, glare, subject's ability to clearly see details, subject's ability to clearly perceive contrasts and colors, the pleasantness of the light, the physical appearance of the lighting fixture and how comfortable the lighting was on the eyes. The subjects' assessment of the filtered lighting produced by the 440 nm pump LED light with the 455-490 nm notch filter was on average very similar to their assessment of unfiltered lighting. The overall preference of filtered vs. unfiltered light varied between individuals and did not show a consistent trend in the 12 studied subjects who participated in this comparison.

The assessment of the filtered lighting produced by the 440 nm pump LED light with the 440 nm pump LED light with sub 500 nm cut off filter was, as expected, quite different and overall judged less favorably (e.g., compromised color perception) than the unfiltered lighting or lighting with a narrow notch filter. This is not surprising because the range of blocked wavelengths was very large with the cut-off filter. This lighting may not be a viable choice for some workplace lighting environments, and its testing was primarily conducted to establish a reference for melatonin preservation under light conditions with extensive filtering.

As illustrated in FIG. 12B, the 440 nm pump LED including a sub 500 nm cut off filter cuts off the bottom of the spectrum of light creating a non-white light that may be undesirable in many work environments. On the other hand, as illustrated in FIG. 12D, The 415 nm pump LED with a 430-500 nm notch filter does create a suitable white light for a working environment in addition to maintaining desirable levels of melatonin in the subjects as demonstrated above and as illustrated in FIG. 15. The final light condition with the 415 nm pump LED light with the 430-500 nm notch filter got better ratings than the lighting with the cut-off filter. Pleasantness and comfort of the 415 nm pump LED light with the 430-500 nm notch filter lighting was rated comparable to the unfiltered lighting and to lighting with narrow-notch filters. Three of the four subjects tested with the 415 nm pump LED light with the 430-500 nm notch filter stated that, assuming that this lighting had positive effects on health and well-being, they would choose this type of lighting over conventional workplace ceiling lighting.

The testing confirmed spectrum-specific LED lighting solutions are capable of preventing circadian disruption associated with nocturnal exposure to traditional lighting. In addition, the results showed that filtered light sources can be effective regarding preserving normal nocturnal melatonin patterns in humans while awake at night. Specifically, the testing showed that lighting produced by 415 nm pump LEDs with a 430-500 nm notch filter is particularly suited to lighting for night shifts as it minimizes exposure to the spectral range responsible for disruption of nocturnal melatonin patterns and provides suitable light for working conditions. It is also contemplated that narrower or different ranges of blocked wavelengths, such as those discussed herein, may further enhance the spectrum of light produced while maintaining the desired melatonin effect and desired conditions for particular environments.

Figure 16:
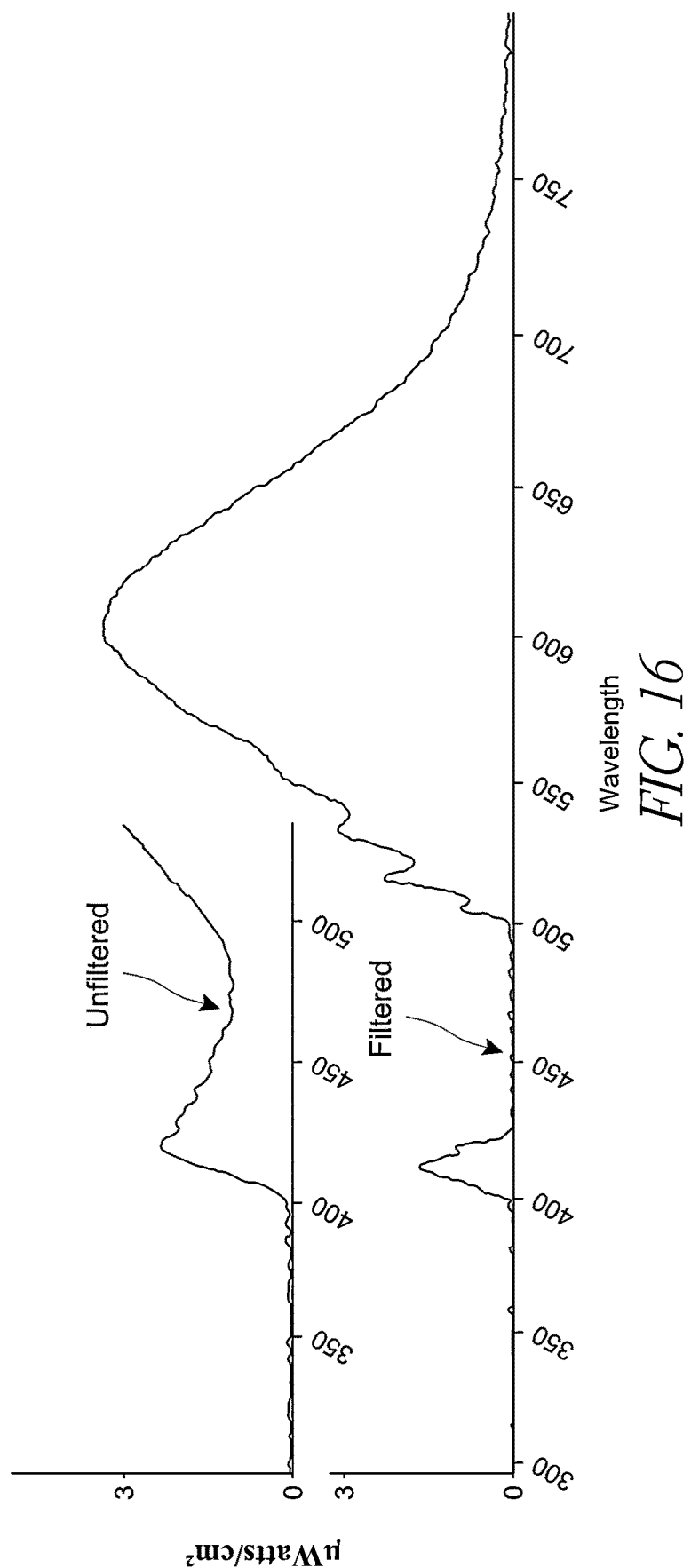
FIG. 16 illustrates the spectra of the unfiltered and filtered Soraa MR16 light source.
Figure 17:
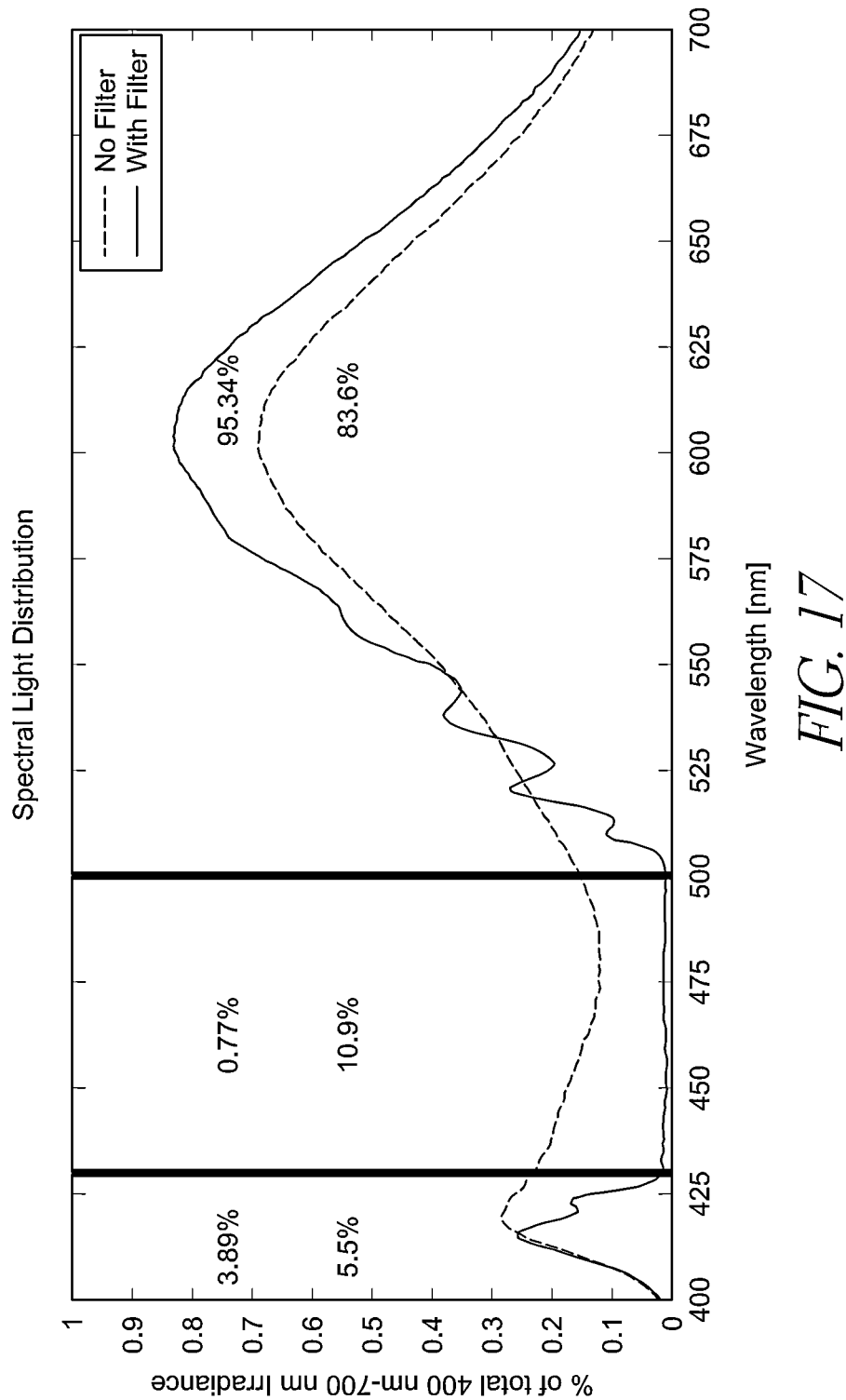
FIG. 17 illustrates percentages of total irradiance in a bioactive band with and without filtering and in the wavelengths of visible light not in the bioactive band.

FIG. 16 illustrates the irradiance measured at approximately 4 feet from the floor for the unfiltered and filtered wavelengths in the bioactive band for a Soraa MR16 light source according to some systems and methods of the disclosure. FIG. 17 illustrates percentages of total irradiance in a bioactive band with and without filtering and in the wavelengths of visible light not in the bioactive band according to some aspects of the disclosure that will be discussed in more detail below.

ADDITIONAL EXAMPLES AND EMBODIMENTS

Exemplary features and aspects of some advantageous systems and methods are further described herein. For example, systems and methods for providing advanced lighting system solutions are described. Systems and methods for providing an effective circadian-modulated spectral distribution pattern are also disclosed. According to some embodiments, systems are arranged and configured in accordance with certain features, aspects and advantages of the present disclosure. The systems are similar in some aspects to other systems described herein. The systems are unique in some aspects as described further herein. Systems and methods can include one or more of the following features and combinations.

According to some advantageous aspects, systems and methods for lighting an area can comprise providing for a specific effective circadian-modulated spectral distribution pattern, such as one or more of the patterns described herein. For example, in some embodiments, systems and methods can comprise a nocturnal spectral distribution pattern with a high violet spike (e.g., about 400-430 nm) and the elimination of, or emission of very low levels of, bioactive blue light (e.g., about 430 nm to 490 nm and/or other alternatives as described herein), and emission of normal levels of about 490 nm to 700 nm visible light wavelengths. For example, in some embodiments, systems and methods can comprise a daytime spectral distribution pattern that has a full 400 nm-700 nm light spectrum with normal or elevated levels of bioactive blue light (e.g., about 430-490 nm).

As used herein, the terms "nocturnal" and "daytime" and/or "day/night" are broad terms and are used herein in their ordinary senses, and, for example, generally refer to different specific circadian phases of the circadian (approximately 24 hour) day, which are determined by circadian (biological) clocks of an individual. They do not necessarily relate to the intervals between sunset and sunrise, or sunrise and sunset. According to some embodiments, the precise times of the 24 hours of the nocturnal and daytime conditions, and the transition waveform used between conditions (e.g., abrupt on-off or gradual like dawn & dusk) when the day and night specifications of light wavelength spectral distribution are switched on and off, can be selected and/or controlled by a user or a manufacturer of the system, and/or can be predetermined or automatically determined by the system.

In some embodiments, a system comprises a luminaire that emits a particular circadian-modulated light wavelength profile. In some embodiments, the luminaire is a lighting fixture. In some embodiments, the luminaire is a light bulb. The system preferably provides defined circadian day/night timed wavelength distributions generated by the luminaire.

In some embodiments, a system comprises mechanically moving filters. For example, in some embodiments, a system uses a single type of violet LED+phosphor chip array (e.g., Soraa GaN on GaN chip array) which generates a full visual light spectrum. During a nocturnal condition, the system is configured to mechanically position optical wavelength filters in relation to the chip array to eliminate or greatly reduce blue light (about 430-490 nm) during the night. After the nocturnal condition, the system is configured to remove the filters to allow the emission of a broad spectrum light including the bioactive blue light wavelengths during the day. In some embodiments a violet spike LED is preferred to obtain a good quality light even when the specific blue wavelengths are filtered out at night. Various types of optical filters can be used. Filters preferably block or sufficiently reduce a particular range of wavelengths of blue light transmission by a defined amount. One or more of the filter ranges described herein can be used as desired. For example, in some embodiments, the filters can be Dichroic (e.g., "reflective" or "thin film" or "interference" filters). In some embodiments, the filters can be absorptive filters. According to some embodiments, the chip array can be a moving part to achieve the day/night timed alternation between unfiltered and filtered light. According to some embodiments, the optical filter can be a moving part to achieve the day/night timed alternation between unfiltered and filtered light. In some embodiments, both the chip array and the optical filter can move to achieve the day/night timed alternation between unfiltered and filtered light.

In some embodiments, a system is arranged and configured to switch between filtered and unfiltered LED+phosphor chips. For example, in some embodiments, a system uses two sets of a single type of violet LED phosphor-coated chip or chip array (e.g., Soraa GaN on GaN chip array) that emits a full light spectrum. One set is preferably equipped with fixed optical wavelength filters and the other set is preferably unfiltered so that the desired day/night pattern is accomplished by switching off the unfiltered chip array at night, and leaving only light emission from the filtered light chip array, according to some embodiments. For example, during the day the filtered set of chips or chip arrays would be switched off, while the unfiltered set is switched on. The LED+phosphor used preferably has a strong peak of emission in the violet wavelengths (about 400-430 nm) to maintain color quality in the set equipped with optical wavelength filters.

In some embodiments, a system is arranged and configured with LED chips that emit light through two channels. For example, one channel is preferably coated with phosphor or a set of phosphors that eliminates or minimizes blue light (e.g., about 430-490 nm) but emits light across other wavelengths (e.g., about 400-430 and about 490-700 nm) and the other channel preferably has little or no phosphor coating and emits blue wavelengths (e.g., about 430-490 nm). According to some embodiments, the system can be configured to use conventional blue-spike LED chips. For example, during the day both channels can be switched on. During the night, preferably only the channel with the phosphor(s) would be switched on.

In some embodiments, a system is arranged and configured with multiple phosphors. For example, in some embodiments, a system preferably uses two sets of a single type of violet LED chip with emission in the non-bioactive (e.g., about 400-430 nm) range. One LED chip set is preferably coated with phosphors which absorb violet light and emit a full visible light spectrum. Another LED chip set is preferably coated with a different phosphor or combinations of phosphors which do not emit light (or greatly reduce light) in a defined blue light range (e.g., about 430-490 nm, about 425-480 nm, etc.) but emit light in about the 490-750 nm range. According to some embodiments, the day/night pattern lighting can be achieved by switching between one set of phosphor coated LEDs to the other set. In some embodiments, alternative coating materials can be used on the violet LED chips which are not conventional rare earth phosphors but have the same or similar absorption and emission characteristics. For example, colloidal quantum dots, or alkyl nanocrystals can replace conventional phosphors (e.g., those placed directly on the chip). Colloidal quantum dot phosphors are nanocrystal emitters and contain no rare-earth elements.

In some embodiments, a system is arranged and configured with RGB type lighting solutions. For example, in some embodiments, systems can use multiple discrete wavelength emitting (monochromatic or near-monochromatic) LED chips which together constitute a full visual light spectrum, (e.g., Violet, Blue, Green, Yellow and Red) and then switch off the blue LED chip during the night, and switching it back on during the day. In some embodiments, these multiple LED based systems might have as few as three discrete LEDs or as many is practical. For example, a system can comprise up to 4, 5, 6, 7, 8, 9, 10, 11, 12, 13, 14, 15, 16, or more color systems in some embodiments. Systems can comprise multiple discrete color channels. In some preferred systems, the LEDs that emit in the blue zone (e.g., about 430-490 nm) can be switched off in the nocturnal state of the lighting system. In some embodiments, Fabry-Pérot interferometers can be used to reduce emissions at the outer edges of the range of emitted light spectrum of the single color LED near the bioactive blue zone (e.g., about 430-490) to create wavelength zones where little or no light is emitted in the target blue wavelengths (e.g., about 430-490 nm) between the single color LED chips.

According to some systems and methods for day/night control of light spectrum, OLED (organic light-emitting diode) based-systems can be used as a source of light emission in the desired wavelengths as opposed to LEDs, with one set of OLEDs providing full-spectrum light and another set of OLEDs emitting light which excludes the bio-active blue wavelengths. For example, OLED systems could replace LEDs in some of the embodiments disclosed herein. In some embodiments, a combination of OLEDs and LEDs can be used.

According to some systems and methods for day/night control of light spectrum, bright (e.g., "sunlight readable") plasma or liquid crystal computer monitor display screen based-systems can be used as a source of light emission in the desired wavelengths with the computer screen programmed to provide full-spectrum light during the day and light which excludes the bio-active blue wavelengths during the night. Other monitors, screens, and/or displays can also be adapted and/or configured as a source of light emission in the desired wavelengths with the monitors, screens, and/or displays programmed to provide full-spectrum light during the day and light which excludes the bio-active blue wavelengths during the night. According to some embodiments, devices with advantageous monitors, screens, and/or displays as described herein include personal computing devices, laptops, tablets, phones, kiosks, televisions, and can include generally stationary devices and portable devices.

In some embodiments, a system comprises wearable filters. For example, in some embodiments, a system uses a single type of violet LED+phosphor chip array (e.g., Soraa GaN on GaN chip array) which generates a full visual light spectrum. During a nocturnal condition, users of the system are provided with wearable filter systems, such as, for example, glasses, goggles, shields and/or other wearable filter configurations that can be used personally to shield a user by positioning optical wavelength filters on a user in an environment of the chip array to eliminate or greatly reduce blue light (about 430-490 nm) during the night. After the nocturnal condition, the user can remove the filters to allow the emission of a broad spectrum light including the bioactive blue light wavelengths during the day. In some embodiments a violet spike LED is preferred to obtain a good quality light even when the specific blue wavelengths are filtered out at night. Various types of wearable and/or personal optical filters can be used. Filters preferably block or sufficiently reduce a particular range of wavelengths of blue light transmission by a defined amount. One or more of the filter characteristics and/or ranges described herein can be used as desired.

In some embodiments, a system is arranged and configured for outdoor lighting applications using filtered night light sources. For example, in some embodiments, a system uses a light source and a filter. The system can have a violet LED phosphor-coated chip or chip array (e.g., Soraa GaN on GaN chip array) that emits a full light spectrum. Other light sources and arrangements as described herein can also be used. The light source is preferably equipped with fixed optical wavelength filter, according to some embodiments. In other embodiments, the desired spectrum of transmitted light can be achieved in any of the ways described herein. For example, during the day the filtered set of chips or chip arrays would typically be switched off. The light source used preferably has a strong peak of emission in the violet wavelengths (about 400-430 nm) to maintain color quality in the set equipped with optical wavelength filters to limit night emissions in the blue wavelengths (e.g., about 430-490 nm). According to some embodiments, outdoor lighting devices with advantageous filtered light sources as described herein include street lights, stadium lights, court lights, vehicle headlights, yard lights, patio lighting, park lighting, amusement park lighting, parking lot and/or structure lighting, flood lights, construction lighting, accent lighting including for lighting architectural structures at night, and other lighting systems suitable for predominantly nighttime lighting uses.

According to some systems and methods for day/night control of light spectrum, other types of wavelength management devices can be used. For example, in some embodiments, an absorber system can be used. An absorber system can be different from an interference filter in that the absorption may not depend on light incidence angle in some embodiments. The absorber can be a phosphor (similar to those discussed herein) or simply an absorber that produces heat alone. In some embodiments, a wavelength management device can comprise an electrochromic material and/or structure to absorb or transmit light in a forbidden zone. In some embodiments, a wavelength management device can comprise a photonic crystal filter element. The photonic crystal preferably is designed with an optical bandgap to limit and/or prevent propagation of light in a forbidden zone. In some embodiments the photonic crystal is a 2D photonic crystal element. In some embodiments the photonic crystal is a 3D photonic crystal element. In some embodiments, a wavelength management device can comprise plasmonic structures designed to absorb light in a forbidden zone. In some embodiments, a wavelength management device can comprise any suitable and/or efficacious combination of wavelength management devices and/or interference filters.

According to some systems and methods, designs can comprise the use of wavelength management devices in and/or on an LED semiconductor element, in an LED package, module, primary optic, secondary and/or tertiary optics, used to make the fixture. According to some systems and methods, designs can comprise the use of wavelength management systems (e.g., absorbers, plasmonics) directly on nominally reflective surfaces in the fixture contacted by radiation from the LEDs and/or LED phosphor combination (for example, where OLED is included as a specific type of LED). According to some systems and methods, designs can comprise the use of wavelength management devices on and/or in waveguide structures (e.g., planar, curved, fiber based) that may be used in the design and operation of a lighting system and/or luminaire.

According to some systems and methods, features for dynamic spectral management can comprise digital and/or analog control of light emission from various groups of LEDs, with or without phosphor, as is needed to dynamically control the spectral density of the light source. According to some systems and methods, features for dynamic spectral management can comprise digital and/or analog control of an electrochromic absorber that may be used to manage the transmission or absorption of light in a forbidden zone. According to some systems and methods, features for dynamic spectral management can comprise a mechanical structure where a combination of absorbers and/or filters can be used to dynamically block and/or transmit light in a forbidden zone. For example, the structure(s) can be in any or all parts (e.g., in various physical configurations) of the primary, secondary and/or tertiary optical system.

According to some systems and methods, one aspect of the present disclosure is the realization that when designing a lighting system to deliver a certain intensity and spectral wavelength composition to the occupants of an artificially illuminated environment such as a workplace, residence or public space it is advantageous to consider and/or define not only the lighting systems and/or luminaires but also the characteristics of that environment.

The quality and intensity of light that reaches a person's eye depends not only on the spectral composition of the light, but can also depend on the material properties of the environmental surfaces, including the color, reflectance and texture. In some applications, quantitative measures of light source emissions may not fully account for the reflective properties of the surfaces in the environment, including the effects of fluorescent dyes and materials.

There are a number of conditions which may be considered when designing and installing light sources to optimize human vision, perception, performance and health. When light strikes a surface, it is reflected, absorbed or transmitted—or a combination of two or three effects may occur. Dark colors, like flat black paint reflect little light and absorb nearly all of the incident light rays, while bright surfaces such as white paint reflects most incident light. When light strikes an opaque surface that will not transmit light, some of the light is absorbed and some reflected. Similarly, smooth surfaces reflect light back but if the surface is not a perfect transmitter, such as a mirror, part of the light will be absorbed and is converted into heat. In addition, different surfaces reflect light in different ways. For example carpet exhibits matt or diffuse reflection where the reflected light is scattered equally in all directions thereby appearing equally bright from any direction.

Accordingly, in some applications, it is therefore advantageous to measure and assess the reflectances of the main surfaces of an environment because their properties may reflect light and either increase or decrease the illuminance within a space.

According to some systems and methods, an artificially illuminated environment system is adapted for one or more people to be situated therein. A defined environment space is provided. An artificial light source is adapted to deliver light within the defined environment space. The artificial light source is configured such that after taking into account any natural light sources present that deliver light within the defined environment space of the artificially illuminated environment, and after taking into account features of any environmental components present within the defined environment space of the artificially illuminated environment, such as optics, spectral reflectivity of surfaces, and/or properties of materials in the defined environment space that fluoresce, the artificial light source in combination with any contributing natural light sources and/or environmental components delivers between about fifty (50) and about two thousand (2,000) lux of light in the visible light range (about 400 nm to about 700 nm) at between about two (2) and about seven (7) feet above a floor level of the defined environment space. A Circadian Night Mode (CNight Mode) in which light is delivered in a selected bioactive wavelength band range preferably does not exceed an average irradiance of about 1 µWatts/cm2 when measured in any direction, wherein the selected bioactive wavelength band range spans at least about 10 nm, and wherein the selected bioactive wavelength band range falls within a general wavelength band range of between about 430 nm and about 500 nm.

The selected bioactive wavelength band range in the CNight Mode can be selected from a group consisting of bioactive wavelength band ranges of: about 430 nm to about 500 nm, about 430 nm to about 490 nm, about 430 nm to about 480 nm, about 430 nm to about 470 nm, about 430 nm to about 460 nm, about 435 nm to about 500 nm, about 435 nm to about 490 nm, about 435 nm to about 480 nm, about 435 nm to about 470 nm, about 435 nm to about 460 nm, about 440 nm to about 500 nm, about 440 nm to about 490 nm, about 440 nm to about 480 nm, about 440 nm to about 470 nm, about 440 nm to about 460 nm, about 450 nm to about 500 nm, about 450 nm to about 490 nm, about 450 nm to about 480 nm, about 450 nm to about 470 nm, about 450 nm to about 460 nm, about 460 nm to about 500 nm, about 460 nm to about 490 nm, about 460 nm to about 480 nm, and about 460 nm to about 470 nm.

The selected bioactive wavelength band range in the CNight Mode preferably does not exceed an average irradiance selected from a group consisting of: about 0.7 µWatts/cm2, about 0.5 µWatts/cm2, about 0.2 µWatts/cm2, and about 0.1 µWatts/cm2, between approximately two (2)-seven (7) feet from the floor, when measured in any direction.

The CNight Mode violet light can be provided in a wavelength band selected from a group consisting of: between about 400 and about 440 nm, between about 400 and about 430 nm, between about 400 and about 425 nm, and between about 400 and about 415 nm, and that has an average irradiance selected from a group consisting of: greater than about 0.5 µWatts/cm2, greater than about 1.0 µWatts/cm2, greater than about 1.5 µWatts/cm2, and greater than about 2.0 µWatts/cm2, between approximately two (2)-seven (7) feet from the floor, when measured in any direction.

The CNight Mode can alternate with a Circadian Day Mode (CDay Mode) that delivers light between about two (2) and about seven (7) feet above the floor level of the defined environment space, and between about fifty (50) and about two thousand (2,000) lux of light with an irradiance in the selected bioactive wavelength band range that is at similar levels to the irradiance of other visible light wavelengths, between approximately two (2)-seven (7) feet from the floor, when measured in any direction.

The system can be configured to transition automatically between the CDay Mode and the CNight Mode in response to predetermined circadian-phase or time of day instructions, and wherein the duration and timing of CDay and the duration and timing of CNight can be preset by the user. The predetermined circadian-phase or time of day instructions can be selected from a group consisting of: instructions including seasonal adjusted times, instructions including fixed clock times, and instructions including times chosen by a user. The environment can be configured based on circadian-phase data, or information, obtained from individuals being illuminated by the artificially illuminated environment system. In some embodiments, the system is configured to transition abruptly between the CDay Mode and the CNight Mode. In some embodiments, the system is configured to transition gradually between the CDay Mode and the CNight Mode.

According to some systems and methods, a lighting system comprises an artificial light source. The artificial light source delivers light in the visible light range (about 400 nm to about 700 nm), and includes a Circadian Night Mode (CNight Mode) in which light delivered in a selected bioactive wavelength band range delivers less than six percent (6%) of the total irradiance from the artificial light source in the visible light range. The selected bioactive wavelength band range can deliver an irradiance selected from a group consisting of: less than six percent (6%), less than four percent (4%), less than two percent (2%), and less than one percent (1%), of the total irradiance from the artificial light source in the visible light range. The CNight Mode violet light is provided in a wavelength band selected from a group consisting of: between about 400 and about 435 nm, between about 400 and about 430 nm, between about 400 and about 425 nm, and between about 400 and about 415 nm, and that has an average irradiance selected from a group consisting of: greater than about four percent (4%), greater than about six percent (6%), and greater than about ten percent (10%), of the total irradiance from the light source in the visible light range. The CNight Mode preferably alternates with a Circadian Day Mode (CDay Mode) wherein the selected bioactive wavelength band range delivers an irradiance selected from a group consisting of: greater than about four percent (4%), greater than about six percent (6%), and greater than about ten percent (10%), of the total irradiance from the light source in the visible light range. The system can be configured to transition automatically between the CDay Mode and the CNight Mode in response to predetermined circadian-phase or time of day instructions. The duration and timing of CDay and the duration and timing of CNight can be preset by the user. The predetermined circadian-phase or time of day instructions may be selected from a group consisting of: instructions including seasonal adjusted times, instructions including fixed clock times, and instructions including times chosen by a user.

In some cases, the artificial light source only delivers light in the CNight Mode. For example, a second light source can deliver light in a Circadian Day Mode (CDay Mode). The second light source can comprise a conventional light source. The second light source may comprise a pre-existing light fixture and/or be installed in parallel with the artificial light source. The artificial light source can be selected from a group consisting of: a ceiling luminaire, a wall luminaire, a desk/table lamp, portable lamps, vehicle lamps, outdoor lamps, screens/monitors of electronic devices. The artificial light source may comprise an LED or a non-LED-based source.

According to some systems and methods, a lighting system comprises a light source. The light source preferably is configured to emit light having a spectral distribution pattern with a violet spike between about 400 nm and about 440 nm. A notch filter can be adapted to be coupled to the light source. The notch filter can be configured to filter light emitted by the light source such that a bioactive wavelength band delivers less than about six percent (6%) of the total irradiance from the light source in the visible light range in a first filtered configuration corresponding to a CNight spectral distribution pattern. A second non-filtered configuration corresponds to a CDay spectral distribution pattern. The bioactive wavelength band can deliver more than about four percent (4%) of the total irradiance from the light source in the visible light range in some embodiments.

The bioactive wavelength band in the CNight spectral distribution pattern can be selected from a group consisting of bioactive wavelength band ranges of: about 430 nm to about 500 nm, about 430 nm to about 490 nm, about 430 nm to about 480 nm, about 430 nm to about 470 nm, about 430 nm to about 460 nm, about 435 nm to about 500 nm, about 435 nm to about 490 nm, about 435 nm to about 480 nm, about 435 nm to about 470 nm, about 435 nm to about 460 nm, about 440 nm to about 500 nm, about 440 nm to about 490 nm, about 440 nm to about 480 nm, about 440 nm to about 470 nm, about 440 nm to about 460 nm, about 450 nm to about 500 nm, about 450 nm to about 490 nm, about 450 nm to about 480 nm, about 450 nm to about 470 nm, about 450 nm to about 460 nm, about 460 nm to about 500 nm, about 460 nm to about 490 nm, about 460 nm to about 480 nm, and about 460 nm to about 470 nm.

The violet spike can be provided in a wavelength band selected from a group consisting of: between about 400 and about 425 nm, between about 400 and about 415 nm, an between about 410 and about 420 nm, and that has an average irradiance selected from a group consisting of: greater than about four percent (4%), greater than about six percent (6%), and greater than about ten percent (10%), of the total irradiance from the light source in the visible light range. The bioactive wavelength band in the CNight spectral distribution pattern delivers an irradiance selected from a group consisting of: less than four percent (4%), less than two percent (2%), and less than one percent (1%), of the total irradiance from the light source in the visible light range. The bioactive wavelength band in the CDay spectral distribution pattern delivers an irradiance selected from a group consisting of: greater than six percent (6%), and greater than 10 percent (10%), of the total irradiance from the light source in the visible light range.

The notch filter is movable relative to the light source which is generally fixed in some embodiments. The light source is movable relative to the notch filter which is generally fixed in some embodiments. The light source and notch filter are independently movable in some embodiments. The light source can comprise a violet pump LED+phosphor chip array. The light source can comprise a GaN on GaN LED+Phosphor chip array. The light source can comprise an OLED. The notch filter can be a dichroic filter. The notch filter is an absorptive filter in some embodiments.

According to some systems and methods, a light source comprises a plurality of discrete wavelength emitting LED chips. The plurality of LED chips together constitute a full visual light spectrum, in a CDay mode. One or more of the discrete wavelength emitting LED chips is configured to be selectively switched off in a CNight mode such that a bioactive wavelength band delivers less than one percent (1%) of the total irradiance from the light source in the visible light range. In some embodiments, a bioactive wavelength band can deliver an irradiance selected from a group consisting of: less than six percent (6%), less than four percent (4%), less than two percent (2%), and less than one percent (1%), of the total irradiance from the light source in the visible light range. One or more of the LED chips can be monochromatic. In some embodiments, one or more of the LED chips are near-monochromatic. The full visual light spectrum preferably comprises discrete wavelength chips for Violet, Blue, Green, Yellow and Red wavelengths in some embodiments. A Blue LED chip is preferably configured to be selectively switched off in the CNight mode.

According to some systems and methods, a light source comprises first and second separately-controlled sets of violet LED chips. The first set of violet LED chips is configured to be switched on in a CDay mode and is coated with phosphors which absorb violet light and emit a visible light spectrum across the 400-700 nm range. The second set of LED chips is configured to be switched on in a CNight mode and is coated with a different phosphor or combinations of phosphors which limit light in a bioactive wavelength band so that the bioactive wavelength band delivers less than one percent (1%) of the total irradiance from the light source in the visible light range. In some embodiments, a bioactive wavelength band can deliver an irradiance selected from a group consisting of: less than six percent (6%), less than four percent (4%), less than two percent (2%), and less than one percent (1%), of the total irradiance from the light source in the visible light range. The day-night pattern lighting can be achieved by switching between the first and second sets of phosphor-coated LEDs. In some embodiments, the coating materials used on the violet LED chips are not conventional rare earth phosphors but have similar absorption and emission characteristics. The coating materials used on the violet LED chips can include colloidal quantum dots and/or alkyl nanocrystals.

According to some systems and methods, a lighting system comprises a light source comprising a plurality of LED chips that emit light through first and second channels. The first channel is coated with a phosphor or set of phosphors that during the CNight mode limits light transmission in a bioactive wavelength band so that the bioactive wavelength band delivers less than one percent (1%) of the total irradiance from the light source in the visible light range. In some embodiments, a bioactive wavelength band can deliver an irradiance selected from a group consisting of: less than six percent (6%), less than four percent (4%), less than two percent (2%), and less than one percent (1%), of the total irradiance from the light source in the visible light range. The second channel is configured to be switched on during the CDay mode and has no phosphor coating. The bioactive wavelength band in the CDay mode delivers more than 4% of the total irradiance from the light source in the visible light range in some embodiments. The bioactive wavelength band in the CDay mode can deliver an irradiance selected from a group consisting of: greater than six percent (6%), and greater than 10 percent (10%), of the total irradiance from the light source in the visible light range.

It should be noted that various changes and modifications to the presently preferred embodiments described herein will be apparent to those skilled in the art. Such changes and modifications may be made without departing from the spirit and scope of the disclosure and without diminishing its attendant advantages. For instance, various components may be repositioned as desired. It is therefore intended that such changes and modifications be included within the scope of the disclosure. Moreover, not all of the features, aspects and advantages are necessarily required to practice the present disclosure. Accordingly, the scope of the present disclosure is intended to be defined only by the claims.

What is claimed is:

1. A device, comprising:
a display configured to emit light; and
a device controller configured to cause the display to emit one or more modes of white light, each mode having a total spectral power in a wavelength range from 400 nm to 700 nm, a first component wavelength range from 400 nm to 430 nm, a second component wavelength range from 430 nm to 500 nm, and a third component wavelength range from 500 nm to 700 nm; and
wherein said one or more modes of white light comprises a first mode wherein greater than four percent (4%) of the total spectral power of said first mode is in said first component wavelength band, and wherein less than six percent (6%) of the total spectral power of said first mode is in said second component wavelength band.

2. The device of claim 1, wherein the display is a liquid crystal display.

3. The device of claim 1, wherein the display is a plasma display.

4. The device of claim 1, wherein the device is a computer display or a television.

5. The device of claim 1, wherein the device is a phone, a tablet or a laptop computer.

6. The device of claim 1, wherein the device comprises one or more light emitting diodes (LEDs) and/or organic light emitting diodes (OLEDs).

7. A device, comprising:
at least one violet light emitting diode (LED);
at least one blue LED;
at least one green LED;
at least one red LED;
a device controller configured to control light emission from the at least one violet LED, at least one blue LED, at least one green LED, and at least one red LED to emit one or more modes of white light, each mode having a total spectral power in a wavelength range from 400 nm to 700 nm, a first component wavelength range from 400 nm to 430 nm, a second component wavelength range from 430 nm to 500 nm, and a third component wavelength range from 500 nm to 700 nm:
wherein said one or more modes of white light comprises a first mode wherein greater than four percent (4%) of the total spectral power of said first mode is in said first component wavelength band, and wherein less than six percent (6%) of the total spectral power of said first mode is in said second component wavelength band.

8. The device of claim 7, wherein the device comprises a LED array comprising the at least one violet LED, at least one blue LED, at least one green LED, and at least one red LED.

9. A method, comprising:
emitting one or more modes of white light from a display, each mode having a total spectral power in a wavelength range from 400 nm to 700 nm, a first component wavelength range from 400 nm to 430 nm, a second component wavelength range from 430 nm to 500 nm, and a third component wavelength range from 500 nm to 700 nm:
wherein said one or more modes of white light comprises a first mode wherein greater than four percent (4%) of the total spectral power of said first mode is in said first component wavelength band, and wherein less than six percent (6%) of the total spectral power of said first mode is in said second component wavelength band.

10. The method of claim 9, wherein the display comprises at least a first light emitting diode (LED) configured to emit light having an intensity peak in the first component wavelength band.

11. The method of claim 10, wherein the display further comprises at least a second LED configured to emit light having an intensity peak in the second component wavelength band and the controller is programmed to vary a relative intensity of the first and second LEDs according to the circadian cycle.

12. The device of claim 1, wherein less than one percent (1%) of the total spectral power of said first mode is in said second component wavelength band.

13. The device of claim 1, wherein greater than then ten percent (10%) of the total spectral power of said first mode is in said first component wavelength band.

14. The device of claim 1, wherein said one or more modes of white light comprises a second mode wherein greater than ten percent (10%) of the total spectral power in said second mode is in the second component wavelength band.

15. The device of claim 14, wherein said first mode is a night mode and said second mode is a day mode.

16. The device of claim 14, wherein said device controller is configured to switch between said first and second modes automatically.

17. The device of claim 16, wherein said device controller is configured to switch between said first and second modes automatically based on predetermined circadian-phase or time of day instructions.

18. The device of claim 17, wherein said predetermined circadian-phase or time of day instructions comprises at least one of seasonal adjusted times, instructions including fixed clock times, and instructions including times chosen by a user.

19. The device of claim 7, wherein less than one percent (1%) of the total spectral power of said first mode is in said second component wavelength band.

20. The device of claim 7, wherein said one or more modes of white light comprises a second mode wherein greater than ten percent (10%) of the total spectral power in said second mode is in the second component wavelength band.

* * * * *